US007655447B2

(12) United States Patent
Jaspers et al.

(10) Patent No.: US 7,655,447 B2
(45) Date of Patent: Feb. 2, 2010

(54) ZSIG33-LIKE POLYNUCLEOTIDES

(75) Inventors: Stephen R. Jaspers, Edmonds, WA (US); Paul O. Sheppard, Granite Falls, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/239,535

(22) Filed: Sep. 26, 2008

(65) Prior Publication Data
US 2009/0156795 A1  Jun. 18, 2009

Related U.S. Application Data

(62) Division of application No. 10/921,371, filed on Aug. 19, 2004, now Pat. No. 7,445,919, which is a division of application No. 09/853,253, filed on May 10, 2001, now Pat. No. 6,897,286.

(60) Provisional application No. 60/203,300, filed on May 11, 2000.

(51) Int. Cl.
C12N 9/00 (2006.01)
C12N 15/00 (2006.01)
C07H 21/04 (2006.01)
C12Q 1/00 (2006.01)
C12P 21/04 (2006.01)

(52) U.S. Cl. .......................... 435/183; 435/440; 435/4; 435/69.1; 435/71.1; 536/23.2; 536/23.4

(58) Field of Classification Search ................ None
See application file for complete search history.

(56) References Cited

U.S. PATENT DOCUMENTS

| 3,978,035 | A | 8/1976 | Wunsch et al. |
| 5,006,469 | A | 4/1991 | Adelman et al. |
| 5,470,830 | A | 11/1995 | Macielag et al. |
| 6,291,653 | B1 | 9/2001 | Sheppard et al. |
| 6,380,158 | B1 | 4/2002 | Sheppard |
| 6,420,521 | B1 | 7/2002 | Sheppard et al. |
| 6,627,729 | B1 | 9/2003 | Sheppard et al. |
| 6,838,438 | B2 | 1/2005 | Sheppard et al. |
| 6,939,690 | B2 | 9/2005 | Sheppard et al. |
| 2003/0176640 | A1 | 9/2003 | Sheppard et al. |

FOREIGN PATENT DOCUMENTS

| EP | 1197496 A1 | 4/2002 |
| WO | 97/21730 | 6/1997 |
| WO | 98/42840 | 10/1998 |
| WO | 00/73454 | 12/2000 |
| WO | 01/07475 | 2/2001 |

OTHER PUBLICATIONS

Pearson et. al., "Molecular Biology of the Peptide Hormone Families," *Gastrointestinal Hormones in Medicine* 22(4): 753-774, Dec. 1993.

Bednarek, M. et. al., "Structure-Function Studies on the New Growth Hormone-Releasing Peptide, Ghrelin: Minimal Sequence of Ghrelin Necessary for Activation of Growth Hormone Secretagogue Receptor 1a," *J. Med. Chem.* 43: 4370-4376, 2000.

Kojima, M. et. al., "Ghrelin is a growth-hormone-releasing acylated peptide from stomach," *Nature* 402(6762): 656-660, Dec. 9, 1999.

Feighner, S. et. al., "Receptor for Motilin Identified in the Human Gastrointestinal System," *Science* 284: 2184-2188, Jun. 1999.

Sheppard et al., U.S. Appl. No. 09/718,803, filed Nov. 22, 2001.

Daikh, D. et ai., "Structure and Expression of the Human Motilin Gene," *DNA* 8(8): 615-621, 1989.

INC2207941, LIFESEQ™ Clone Information Results, Incyte Pharmaceuticals Inc., 1996.

INC1328219, LIFESEQ™ Clone Information Results, Incyte Pharmaceuticals Inc., 1996.

INC2209486, LIFESEQ™ Clone Information Results, Incyte Pharmaceuticals Inc., 1996.

INC1851527, LIFESEQ™ Clone Information Results, Incyte Pharmaceuticals Inc., 1996.

INC891710, LIFESEQ™ Clone Information Results, Incyte Pharmaceuticals Inc., 1996.

INC1329031, LIFESEQ™ Clone Information Results, Incyte Pharmaceuticals Inc., 1996.

Clone 1329031, LIFESEQ™ Electronic Northern Results, Incyte Pharmaceuticals Inc., 1996.

PANCNOT07, LIFESEQ™ Library Information Results, Incyte Pharmaceuticals Inc., 1996.

LUNGFET03, LIFESEQ™ Library Information Results, Incyte Pharmaceuticals Inc., 1996.

STOMTUT01, LIFESEQ™ Library Information Results, Incyte Pharmaceuticals Inc., 1996.

SINTFET03, LIFESEQ™ Library Information Results, Incyte Pharmaceuticals Inc., 1996.

Accession No. AA530994, Cancer Genome Anatomy Project, 1997.

FLN1329031CB1, LIFESEQ™ Clone Information Results, Incyte Pharmaceuticals Inc., year unknown.

LIN1328219R, LIFESEQ™ Clone Information Results, Incyte Pharmaceuticals Inc., year unknown.

LIN1328219F, LIFESEQ™ Clone Information Results, Incyte Pharmaceuticals Inc., year unknown.

INC3663175, LIFESEQ™ Clone Information Results, Incyte Pharmaceuticals Inc., 1997.

INC3666305, LIFESEQ™ Clone Information Results, Incyte Pharmaceuticals Inc., 1997.

INC3605169, LIFESEQ™ Clone Information Results, Incyte Pharmaceuticals Inc., 1997.

LUNGNOT30, LIFESEQ™ Library Information Results, Incyte Pharmaceuticals Inc., 1997.

PANCNOT16, LIFESEQ™ Library Information Results, Incyte Pharmaceuticals Inc., 1997.

(Continued)

*Primary Examiner*—Yong D Pak
(74) *Attorney, Agent, or Firm*—Robyn Adams

(57) ABSTRACT

The present invention relates to polynucleotide related to the zsig33 peptide, including agonists, antagonists, and antibodies. Methods of modulating gastric contractility, nutrient uptake, growth hormones, the secretion of digestive enzymes and hormones, and/or secretion of enzymes and/or hormones in the pancreas are also included.

25 Claims, No Drawings

OTHER PUBLICATIONS

Miller, P. et al., "Structure-Function Studies of Motilin Analogues," *Peptides* 16(1): 11-18, 1995.

Peeters, T. et al., "D-Amino Acid and Alanine Scans of the Bioactive Portion of Porcine Motilin," *Peptides* 13: 1103-1107, 1992.

Macielag, M. J. et al., "Substitution of Pro[3] in (Leu[13])Motilin Affords Antagonist to the GI Motilin Receptor," *Peptides: Chemistry, Structure and Biology*: 659-660, 1996.

Rhee, S. G. et al., "Regulation of Phosphoinositide-specific Phospholipase C Isozymes," *J. Biol. Chem.* 272(24): 15045-15048, 1997.

Bowie, J. et al., "Deciphering the Message in Protein Sequences: Tolerance to Amino Acid Substitutions," *Science* 247: 1306-1310, 1990.

George, D. et al., "Current Methods in Sequence Comparison and Analysis," *Macromolecular Sequencing and Synthesis, Selected Methods and Applications*: 127-149, 1988.

Barton, G., "Protein Structure Prediction: A Practical Approach," *IRL Press at Oxford Univ.*: 31-63, 1997.

Harlow, E. et al., "Antibodies: A Laboratory Manual" *Cold Spring Harbor*, 1988.

Benjannini, E. et al., "Immunology: A Short Course 2nd ed.," *A John Wiley & Sones, Inc. Publication*: 40, 1991.

Alberts, B. et al., "Molecular Biology of the Cell 3rd ed.," *Garland Publishing, Inc.*: 119, 1994.

Daniel, C. et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity is Drastically Influenced by the Nature of the Protein Carrier," *Virology* 202:540-549, 1994.

Nataro, J. et al., "Aggregative Adherence Fimbria I Expression in Enteroaggregative *Escherichia coli* Requires Two Unlinked Plasmid Regions," *Infection and Immunity* 61(3): 1126-1131, Mar. 1993.

Sambrook, J. et al., "Molecular Cloning: A Laboratory Manual 2nd ed.," *Cold Spring Harbor Laboratory Press*: 18.2-18.10, 1989.

Ngo, J. T. et al., "Computational Complexity, Protein Structure Prediction, and the Levinthal Paradox," *The Protein Folding Problem and Tertiary Structure Prediction*: 492-495, 1994.

Kai, Y. et al., "Studies on Peptides, Total Synthesis of Porcine Motilin, a Gastric Motor Activity Stimulating Polypeptide," *Chem. Pharm. Bull.* 23(10): 2346-2352, 1975.

Sakai, T. et al., "Autoradiographic study of motilin binding sites in the rabbit gastrointestinal tract," *Regulatory Peptides* 53: 249-257, 1994.

Bormans, V. et al., "Motilin receptors in rabbit stomach and small intestine," *Regulatory Peptides* 15: 143-153, 1986.

Hasler, W. et al., "Erythromycin contracts rabbit colon myocytes via occupation of motilin receptors," *Am. J. Physiol.* 262: G50-G55, 1992.

Depoortere, I. et al., "Motilin Receptors of the Rabbit Colon," *Peptides* 12: 89-94, 1991.

Koutsoviti-Papadopoulou, M. et al., "Effect of Erythromycin on Difference Parts of the Rabbit Intestine: Comparison with Motilin," *Gen. Pharmac.* 25(1): 93-96, 1994.

Rehfeld, J. et al., "Characterization of Preprocholecystokinin Products in the Porcine Cerebral Cortex," *J. Biol. Chem.* 261(13): 5832-5840, May 1986.

Rehfeld, J. et al., "Identification of gastrin component I as gastrin-71," *Eur. J. Biochem.* 223: 765-773, 1994.

Franks, F., "Protein Biotechnology: Isolation, Characterization, and Stabilization," *Humana Press*, 1993.

Beacham, J. et al., "Gastrins from Some Mammalian Species," *Peptides, North-Holland Publishing Company*: 235-241, 1967.

Christ, A. et al., "Human Secretin, Biologic Effects and Plasma Kinetics in Humans," *Gastroenterology* 94: 311-316, 1988.

Cunningham, B. et al., "High-Resolution Epitope Mapping of hGH-Receptor Interactions by Alanine-Scanning Mutagensis," *Science* 244: 1081-1085, Jun. 1989.

Drucker, D. J., "Glucagon and the Glucagon-Like Peptides," *Pancreas* 5(4): 484-488, 1990.

Schwartz, T. W., "Cellular Peptide Processing After a Single Arginyl Residue Studies on the Common Precursor for Pancreatic Polypeptide and Pancreatic Icosapeptide," *J. Biological Chemistry* 262(11): 5093-5099, 1987.

Huang,Z. et al., "Sequence and characterization of cDNA encoding the motilin precursor from chicken, dog, cow and horse. Evidence of mosaic evoluation in prepromotilin," *Gene* 240(1): 217-226, Nov. 15, 1999.

Sheppard et al., U.S. Appl. No. 12/147,187, filed Jun. 26, 2008.

SEQUENCE LISTING

<160> NUMBER OF SEQ ID NOS: 28

<210> SEQ ID NO 1
<211> LENGTH: 527
<212> TYPE: DNA
<213> ORGANISM: Homo sapiens
<220> FEATURE:
<221> NAME/KEY: CDS
<222> LOCATION: (50)...(400)

<400> SEQUENCE: 1

```
gaattcggct cgagctgcag gcccacctgt ctgcaaccca gctgaggcc atg ccc tcc      58
                                                     Met Pro Ser
                                                      1 cca ggg acc gtc tgc agc ctc ctg ctc ctc ggc atg ctc tgg ctg gac     106
Pro Gly Thr Val Cys Ser Leu Leu Leu Leu Gly Met Leu Trp Leu Asp
     5                  10                  15 ttg gcc atg gca ggc tcc agc ttc ctg agc cct gaa cac cag aga gtc     154
Leu Ala Met Ala Gly Ser Ser Phe Leu Ser Pro Glu His Gln Arg Val
 20                  25                  30                  35 cag cag aga aag gag tcg aag aag cca cca gcc aag ctg cag ccc cga     202
Gln Gln Arg Lys Glu Ser Lys Lys Pro Pro Ala Lys Leu Gln Pro Arg
                 40                  45                  50 gct cta gca ggc tgg ctc cgc ccg gaa gat gga ggt caa gca gaa ggg     250
Ala Leu Ala Gly Trp Leu Arg Pro Glu Asp Gly Gly Gln Ala Glu Gly
             55                  60                  65 gca gag gat gaa ctg gaa gtc cgg ttc aac gcc ccc ttt gat gtt gga     298
Ala Glu Asp Glu Leu Glu Val Arg Phe Asn Ala Pro Phe Asp Val Gly
         70                  75                  80 atc aag ctg tca ggg gtt cag tac cag cag cac agc cag gcc ctg ggg     346
Ile Lys Leu Ser Gly Val Gln Tyr Gln Gln His Ser Gln Ala Leu Gly
     85                  90                  95 aag ttt ctt cag gac atc ctc tgg gaa gag gcc aaa gag gcc cca gcc     394
Lys Phe Leu Gln Asp Ile Leu Trp Glu Glu Ala Lys Glu Ala Pro Ala
100                 105                 110                 115 gac aag tgatcgccca caagccttac tcacctctct ctaagtttag aagcgctcat      450
Asp Lys ctggcttttc gcttgcttct gcagcaactc ccacgactgt tgtacaagct caggaggcga      510
ataaatgttc aaactgt                                                    527
```

<210> SEQ ID NO 2
<211> LENGTH: 117

<212> TYPE: PRT
<213> ORGANISM: Homo sapiens

<400> SEQUENCE: 2

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
            20                  25                  30

Gln Arg Val Gln Gln Arg Lys Glu Ser Lys Lys Pro Pro Ala Lys Leu
        35                  40                  45

Gln Pro Arg Ala Leu Ala Gly Trp Leu Arg Pro Glu Asp Gly Gly Gln
    50                  55                  60

Ala Glu Gly Ala Glu Asp Glu Leu Glu Val Arg Phe Asn Ala Pro Phe
65                  70                  75                  80

Asp Val Gly Ile Lys Leu Ser Gly Val Gln Tyr Gln His Ser Gln
            85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 3
<211> LENGTH: 72
<212> TYPE: DNA
<213> ORGANISM: Homo sapiens
<220> FEATURE:
<221> NAME/KEY: CDS
<222> LOCATION: (1)...(72)

<400> SEQUENCE: 3 gct cta gca ggc tgg ctc cgc ccg gaa gat gga ggt caa gca gaa ggg     48
Ala Leu Ala Gly Trp Leu Arg Pro Glu Asp Gly Gly Gln Ala Glu Gly
1               5                   10                  15 gca gag gat gaa ctg gaa gtc cgg                                     72
Ala Glu Asp Glu Leu Glu Val Arg
            20

<210> SEQ ID NO 4
<211> LENGTH: 24
<212> TYPE: PRT
<213> ORGANISM: Homo sapiens

<400> SEQUENCE: 4

Ala Leu Ala Gly Trp Leu Arg Pro Glu Asp Gly Gly Gln Ala Glu Gly
1               5                   10                  15

Ala Glu Asp Glu Leu Glu Val Arg
            20

<210> SEQ ID NO 5
<211> LENGTH: 23
<212> TYPE: PRT
<213> ORGANISM: Homo sapiens

<400> SEQUENCE: 5

Ala Leu Ala Gly Trp Leu Arg Pro Glu Asp Gly Gly Gln Ala Glu Gly
1               5                   10                  15

Ala Glu Asp Glu Leu Glu Val
            20

<210> SEQ ID NO 6
<211> LENGTH: 23

```
<212> TYPE: PRT
<213> ORGANISM: Homo sapiens
<220> FEATURE:
<221> NAME/KEY: AMIDATION
<222> LOCATION: (23)...(23)

<400> SEQUENCE: 6

Ala Leu Ala Gly Trp Leu Arg Pro Glu Asp Gly Gly Gln Ala Glu Gly
1               5                   10                  15

Ala Glu Asp Glu Leu Glu Val
            20

<210> SEQ ID NO 7
<211> LENGTH: 72
<212> TYPE: DNA
<213> ORGANISM: Artificial Sequence
<220> FEATURE:
<223> OTHER INFORMATION: Computationally-derived degenerate nucleotide
      sequence
<221> NAME/KEY: misc_feature
<222> LOCATION: 3, 6, 9, 12, 18, 21, 24, 33, 36, 42, 48, 51, 63, 69, 72
<223> OTHER INFORMATION: n = A,T,C or G

<400> SEQUENCE: 7
gcnytngcng gntggytnmg nccngargay ggnggncarg cngarggngc ngargaygar     60
ytngargtnm gn                                                        72

<210> SEQ ID NO 8
<211> LENGTH: 75
<212> TYPE: DNA
<213> ORGANISM: Homo sapiens
<220> FEATURE:
<221> NAME/KEY: CDS
<222> LOCATION: (1)...(75)

<400> SEQUENCE: 8 ttc aac gcc ccc ttt gat gtt gga atc aag ctg tca ggg gtt cag tac     48
Phe Asn Ala Pro Phe Asp Val Gly Ile Lys Leu Ser Gly Val Gln Tyr
1               5                   10                  15 cag cag cac agc cag gcc ctg ggg aag                                  75
Gln Gln His Ser Gln Ala Leu Gly Lys
            20                  25

<210> SEQ ID NO 9
<211> LENGTH: 25
<212> TYPE: PRT
<213> ORGANISM: Homo sapiens

<400> SEQUENCE: 9

Phe Asn Ala Pro Phe Asp Val Gly Ile Lys Leu Ser Gly Val Gln Tyr
1               5                   10                  15

Gln Gln His Ser Gln Ala Leu Gly Lys
            20                  25

<210> SEQ ID NO 10
<211> LENGTH: 24
<212> TYPE: PRT
<213> ORGANISM: Homo sapiens

<400> SEQUENCE: 10

Phe Asn Ala Pro Phe Asp Val Gly Ile Lys Leu Ser Gly Val Gln Tyr
1               5                   10                  15

Gln Gln His Ser Gln Ala Leu Gly
            20
```

```
<210> SEQ ID NO 11
<211> LENGTH: 23
<212> TYPE: PRT
<213> ORGANISM: Homo sapiens
<220> FEATURE:
<221> NAME/KEY: AMIDATION
<222> LOCATION: (23)...(23)

<400> SEQUENCE: 11

Phe Asn Ala Pro Phe Asp Val Gly Ile Lys Leu Ser Gly Val Gln Tyr
 1               5                  10                  15

Gln Gln His Ser Gln Ala Leu
            20

<210> SEQ ID NO 12
<211> LENGTH: 75
<212> TYPE: DNA
<213> ORGANISM: Artificial Sequence
<220> FEATURE:
<223> OTHER INFORMATION: Computationally-derived degenerate nucleotide
      sequence
<221> NAME/KEY: misc_feature
<222> LOCATION: 9, 12, 21, 24, 33, 36, 39, 42, 60, 66, 69, 72
<223> OTHER INFORMATION: n = A,T,C or G

<400> SEQUENCE: 12
ttyaaygcnc cnttygaygt nggnathaar ytnwsnggng tncartayca rcarcaywsn      60
cargcnytng gnaar                                                      75

<210> SEQ ID NO 13
<211> LENGTH: 51
<212> TYPE: DNA
<213> ORGANISM: Homo sapiens
<220> FEATURE:
<221> NAME/KEY: CDS
<222> LOCATION: (1)...(51)

<400> SEQUENCE: 13 ttt ctt cag gac atc ctc tgg gaa gag gcc aaa gag gcc cca gcc gac      48
Phe Leu Gln Asp Ile Leu Trp Glu Glu Ala Lys Glu Ala Pro Ala Asp
 1               5                  10                  15 aag                                                                   51
Lys

<210> SEQ ID NO 14
<211> LENGTH: 17
<212> TYPE: PRT
<213> ORGANISM: Homo sapiens

<400> SEQUENCE: 14

Phe Leu Gln Asp Ile Leu Trp Glu Glu Ala Lys Glu Ala Pro Ala Asp
 1               5                  10                  15

Lys

<210> SEQ ID NO 15
<211> LENGTH: 16
<212> TYPE: PRT
<213> ORGANISM: Homo sapiens

<400> SEQUENCE: 15

Phe Leu Gln Asp Ile Leu Trp Glu Glu Ala Lys Glu Ala Pro Ala Asp
 1               5                  10                  15

<210> SEQ ID NO 16
```

-continued

```
<211> LENGTH: 16
<212> TYPE: PRT
<213> ORGANISM: Homo sapiens
<220> FEATURE:
<221> NAME/KEY: AMIDATION
<222> LOCATION: (16)...(16)

<400> SEQUENCE: 16

Phe Leu Gln Asp Ile Leu Trp Glu Glu Ala Lys Glu Ala Pro Ala Asp
1               5                   10                  15

<210> SEQ ID NO 17
<211> LENGTH: 15
<212> TYPE: PRT
<213> ORGANISM: Homo sapiens
<220> FEATURE:
<221> NAME/KEY: AMIDATION
<222> LOCATION: (15)...(15)

<400> SEQUENCE: 17

Phe Leu Gln Asp Ile Leu Trp Glu Glu Ala Lys Glu Ala Pro Ala
1               5                   10                  15

<210> SEQ ID NO 18
<211> LENGTH: 51
<212> TYPE: DNA
<213> ORGANISM: Artificial Sequence
<220> FEATURE:
<223> OTHER INFORMATION: Computationally-derived degenerate nucleotide
      sequence
<221> NAME/KEY: misc_feature
<222> LOCATION: 6, 18, 30, 39, 42, 45
<223> OTHER INFORMATION: n = A,T,C or G

<400> SEQUENCE: 18
ttyytncarg ayathytntg ggargargcn aargargcnc cngcngayaa r            51

<210> SEQ ID NO 19
<211> LENGTH: 30
<212> TYPE: DNA
<213> ORGANISM: Homo sapiens
<220> FEATURE:
<221> NAME/KEY: CDS
<222> LOCATION: (1)...(30)

<400> SEQUENCE: 19 ttc aac gcc ccc ttt gat gtt gga atc aag                            30
Phe Asn Ala Pro Phe Asp Val Gly Ile Lys
1               5                   10

<210> SEQ ID NO 20
<211> LENGTH: 10
<212> TYPE: PRT
<213> ORGANISM: Homo sapiens

<400> SEQUENCE: 20

Phe Asn Ala Pro Phe Asp Val Gly Ile Lys
1               5                   10

<210> SEQ ID NO 21
<211> LENGTH: 9
<212> TYPE: PRT
<213> ORGANISM: Homo sapiens

<400> SEQUENCE: 21

Phe Asn Ala Pro Phe Asp Val Gly Ile
1               5
```

```
<210> SEQ ID NO 22
<211> LENGTH: 9
<212> TYPE: PRT
<213> ORGANISM: Homo sapiens
<220> FEATURE:
<221> NAME/KEY: AMIDATION
<222> LOCATION: (9)...(9)

<400> SEQUENCE: 22

Phe Asn Ala Pro Phe Asp Val Gly Ile
 1               5

<210> SEQ ID NO 23
<211> LENGTH: 30
<212> TYPE: DNA
<213> ORGANISM: Artificial Sequence
<220> FEATURE:
<223> OTHER INFORMATION: Computationally-derived degenerate nucleotide
      sequence
<221> NAME/KEY: misc_feature
<222> LOCATION: 9, 12, 21, 24
<223> OTHER INFORMATION: n = A,T,C or G

<400> SEQUENCE: 23
ttyaaygcnc cnttygaygt nggnathaar                                    30

<210> SEQ ID NO 24
<211> LENGTH: 45
<212> TYPE: DNA
<213> ORGANISM: Homo sapiens
<220> FEATURE:
<221> NAME/KEY: CDS
<222> LOCATION: (1)...(45)

<400> SEQUENCE: 24 ctg tca ggg gtt cag tac cag cag cac agc cag gcc ctg ggg aag        45
Leu Ser Gly Val Gln Tyr Gln Gln His Ser Gln Ala Leu Gly Lys
 1               5                  10                  15

<210> SEQ ID NO 25
<211> LENGTH: 15
<212> TYPE: PRT
<213> ORGANISM: Homo sapiens

<400> SEQUENCE: 25

Leu Ser Gly Val Gln Tyr Gln Gln His Ser Gln Ala Leu Gly Lys
 1               5                  10                  15

<210> SEQ ID NO 26
<211> LENGTH: 13
<212> TYPE: PRT
<213> ORGANISM: Homo sapiens
<220> FEATURE:
<221> NAME/KEY: AMIDATION
<222> LOCATION: (13)...(13)

<400> SEQUENCE: 26

Leu Ser Gly Val Gln Tyr Gln Gln His Ser Gln Ala Leu
 1               5                  10

<210> SEQ ID NO 27
<211> LENGTH: 45
<212> TYPE: DNA
<213> ORGANISM: Artificial Sequence
<220> FEATURE:
<223> OTHER INFORMATION: Computationally-derived degenerate nucleotide
      sequence
<221> NAME/KEY: misc_feature
```

-continued

```
<222> LOCATION: 3, 6, 9, 12, 30, 36, 39, 42
<223> OTHER INFORMATION: n = A,T,C or G

<400> SEQUENCE: 27
ytnwsnggng tncartayca rcarcaywsn cargcnytng gnaar          45

<210> SEQ ID NO 28
<211> LENGTH: 6
<212> TYPE: PRT
<213> ORGANISM: Artificial Sequence
<220> FEATURE:
<223> OTHER INFORMATION: Glu-Glu (CEE) tag amino acid sequence

<400> SEQUENCE: 28

Glu Tyr Met Pro Met Glu
 1               5
```

ZSIG33-LIKE POLYNUCLEOTIDES

CROSS-REFERENCE TO RELATED APPLICATIONS

This application is a divisional of U.S. application Ser. No. 10/921,371, filed Aug. 19, 2004, now U.S. Pat. No. 7,445,919 which is herein incorporated by reference, and which is a divisional of U.S. application Ser. No. 09/853,253, filed May 10, 2001, now U.S. Pat. No. 6,897,286, which is herein incorporated by reference, and which claims the benefit of U.S. Provisional Application Ser. No. 60/203,300 filed on May 11, 2000.

BACKGROUND OF THE INVENTION

Many of the regulatory peptides that are important in maintaining nutritional homeostasis are found in the gastrointestinal environment. These peptides may be synthesized in the digestive system and act locally, but can also be identified in the brain as well. In addition, the reverse is also found, i.e., peptides are synthesized in the brain, but found to regulate cells in the gastrointestinal tract. This phenomenon has been called the "brain-gut axis" and is important for signaling satiety, regulating body temperature and other physiological processes that require feedback between the brain and gut.

The gut peptide hormones include gastrin, cholecystokinin (CCK), glucagon, secretin, gastric inhibitory peptide (GIP), vasoactive intestinal polypeptide (VIP), motilin, somatostatin, pancreatic peptide (PP), substance P and neuropeptide Y (NPY), and use several different mechanisms of action. For example, gastrin, motilin and CCK function as endocrine- and neurocrine-type hormones. Others, such as gastrin and GIP, are thought to act exclusively in an endocrine fashion. Other modes of action include a combination of endocrine, neurocrine and paracrine action (somatostatin); exclusively neurocrine action (NPY); and a combination of neurocrine and paracrine actions (VIP and Substance P). Most of the gut hormone actions are mediated by membrane-bound receptors and activate second messenger systems. For a review of gut peptides see, Mulvihill et al., in *Basic and Clinical Endocrinology*, pp. 551-570, 4th edition Greenspan F. S, and Baxter, J. D. editors., Appleton & Lange: Norwalk, Conn., 1994.

Many of these gut peptides are synthesized as inactive precursor molecules that require multiple peptide cleavages to be activated. The family known as the "glucagon-secretin" family, which includes VIP, gastrin, secretin, motilin, glucagon and galanin, exemplifies peptides regulated by multiple cleavages and post-translational modifications.

Motilin is a 22 amino acid peptide found in gut tissue of mammalian species (Domschke, W., *Digestive Diseases* 22(5):454-461, 1977). The DNA and amino acid sequences for porcine prepromotilin have been identified (U.S. Pat. No. 5,006,469). Motilin has been characterized as a factor capable of increasing gastric motility, affecting the secretory function of the stomach by stimulating pepsin secretion (Brown et al., *Canadian J. of Physiol. Pharmacol.* 49:399-405, 1971), and recent evidence suggests a role in myoelectric regulation of stomach and small intestine. Cyclic increases of motilin have been correlated with phase III of the interdigestive myoelectric complex and the hunger contraction of the duodenum (Chey et al., in *Gut Hormones*, (eds.) Bloom, S. R., pp. 355-358, Edinburgh, Churchill Livingstone, 1978; Lee et al, *Am. J. Digestive Diseases,* 23:789-795, 1978; and Itoh et al., *Am. J. Digestive Diseases,* 23:929-935, 1978). Motilin and analogues of motilin have been demonstrated to produce contraction of gastrointestinal smooth muscle, but not other types of smooth muscle cells (Strunz et al., *Gastroenterology* 68:1485-1491, 1975).

The present invention is directed to a novel peptide fragment, and the DNA segment encoding it, of a previously described secreted protein, zsig33 (Sheppard, WO98/42840: 1998). The present invention is also directed to a limited number of variants of said peptide fragment. The discovery of this novel peptide fragment is important for further elucidation of the how the body maintains its nutritional homeostasis and development of therapeutics to intervene in those processes, as well as other uses that will be apparent from the teachings herein.

SUMMARY OF THE INVENTION

The present invention relates to novel Zsig33-like peptides, which are produced by peptide cleavage from the C terminal peptide of zsig33. Within one aspect the invention provides an isolated polypeptide selected from the group consisting of: a polypeptide consisting of the amino acid sequence as shown in SEQ ID NOs:4, 5, or 6; a polypeptide consisting of the amino acid sequence as shown in SEQ ID NOs:9, 10, or 11; a polypeptide consisting the amino acid sequence as shown in SEQ ID NOs:14, 15, 16, or 17; a polypeptide consisting the amino acid sequence as shown in SEQ ID NOs:20, 21, or 22; and a polypeptide consisting the amino acid sequence as shown in SEQ ID NOs:25, 26, or 27. Within an embodiment is provided an isolated polynucleotide encoding said isolated polypeptide. Within another embodiment the invention provides a method of binding said isolated polypeptide. Within another embodiment, the invention provides a method of modulating contractility in gastrointestinal tissue comprising applying the isolated polypeptide to gastrointestinal tissue. Within another embodiment the invention provides a method of modulating pancreatic secretion of hormones and digestive enzymes comprising administering the isolated polypeptide to a mammal.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:79524, 1985), substance P, Flag™ peptide (Hopp et al., *Biotechnology* 6:1204-1210, 1988), streptavidin binding peptide, maltose binding protein (Guan et al., *Gene* 67:21-30, 1987), cellulose binding protein, thioredoxin, ubiquitin, T7 polymerase, or other antigenic epitope or binding domain. See, in general, Ford et al., *Protein Expression and Purification* 2: 95-107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "complement" of a polynucleotide molecule is a polynucleotide molecule having a complementary base sequence and reverse orientation as compared to a reference sequence. For example, the sequence 5' ATGCAC 3' is complementary to 5' GTGCAT 3'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985)

An "isolated" polypeptide or protein is a polypeptide or protein that is found in a condition other than its native environment, such as apart from blood and animal tissue. In a preferred form, the isolated polypeptide or protein is substantially free of other polypeptides or proteins, particularly those of animal origin. It is preferred to provide the polypeptides and proteins in a highly purified form, i.e. greater than 95% pure, more preferably greater than 99% pure. When used in this context, the term "isolated" does not exclude the presence of the same polypeptide or protein in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "ortholog" denotes a polypeptide or protein obtained from one species that is the functional counterpart of a polypeptide or protein from a different species. Sequence differences among orthologs are the result of speciation.

A "peptide-receptor complex" is formed when a peptide, or ligand, binds to a receptor resulting in a change in the properties of the receptor. This change can result in an initiation of a cascade of reactions leading to a change in cellular function, or the inability of the receptor to bind additional peptides. The forming of a peptide-receptor complex can be reversible.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. thus, a protein "consisting of", for example, from 15 to 1500 amino acid residues may further contain one or more carbohydrate chains.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of novel peptide fragments of a previously described secreted polypeptide known as zsig33 (Sheppard, WO 98/42840). Zsig33 (shown in SEQ ID NOs: 1 and 2) which has homology to motilin has been found to be transcribed in the gastrointestinal system. The novel peptide fragments (shown in SEQ ID NOs:4-6, 9-11, 14-17, 20-22, and 25-26) have been designated zsig-33-linker, zsig33-beta, zsig33-gamma, zsig33-delta and zsig33-epsilon peptides, herein referred to as zsig33-like peptides (ZS33LPs). Motilin is member of a family of polypeptides that regulate the gastrointestinal physiology. The family of polypeptides important in gastrointestinal regulation to which motilin belongs includes glucagon, gastrin, galanin, and vasoactive intestinal peptide (VIP). These polypeptides are synthesized in a precursor form that requires multiple steps of processing to the active form. Particularly relevant to the peptide of the present invention are motilin, glucagons, VIP and galanin, where processing involves removal of signal sequence, followed by cleavage of one or more accessory peptides. In the case of glucagon, for example, multiple active peptides result form these cleavages. See Drucker, D., *Pancreas* 5:484-488, 1990. The resulting active peptides are generally small (10-30 amino acids) and may require further post-translational modifications, such as amidation, sulfation acylation, octanoylation, or pyrrolidine carboxylic acid modification of glutamine residues to form pyroglutamic acid.

Analysis of the tissue distribution of the mRNA corresponding to the zsig33 protein showed that expression is highest in stomach, followed by apparent but decreased expression levels in small intestine and pancreas. The EST for the secreted zsig33 protein is derived from a pancreatic library, and has been shown in lung cDNA libraries. Thus, the novel zsig33-beta and zsig33-gamma peptides would be expected to localize to these tissues or to any other tissues accessible by the circulatory system of the body.

Many of the gut-brain peptides require multiple cleavages. For example, progastrin peptide is 101 amino acids, and is cleaved at the N-terminus resulting in sequentially smaller peptides (G34, G17 and G14) (Sugano et al., *J. Biol. Chem.* 260:11724-11729, 1985). Other peptides that require multiple processing steps include glucagon, for which C-terminal cleavages result in glucagon-like peptide 1 and glucagon-like peptide 2 and galanin, in which processing involves cleavage of a C-terminal peptide known as GMAP.

The ZS33LPs can modulate the absorption of glucose. Factors affecting this modulation can include secretion of digestive enzymes or hormones in organs and tissues involved in the gastrointestinal tract. An assay to measure the absorption of glucose is shown in Example 12.

Molecules of the present invention are related to additional cleavage products of the C terminal peptide which result from monobasic amino acid cleavages at positions 51 (Arg), 75 (Arg), 85 (Lys) and 100 (Lys) of SEQ ID NO: 2. The resultant peptides are designated: zsig33-linker peptide, as shown in SEQ ID NOs:4-6; zsig33-beta peptide, as shown in SEQ ID NOs:9-11; zsig33-gamma peptide, as shown in SEQ ID NOs: 14-17; zsig33-delta peptide, as shown in SEQ ID NOs:20-22; and zsig33-epsilon peptide, as shown in SEQ ID NOs:25-26. Glucagon, another gut peptide hormone has similar post-translational processing. See Drucker, D., *Pancreas* 5: 484-488, 1990. One skilled in the art will recognize that such boundaries are approximate and may vary by +/−4 amino acids.

Polypeptides of the present invention comprise at least 6, preferably at least 9, more preferably at least 15 contiguous amino acid residues of SEQ ID NOs:4-6, 9-11, 14-17, 20-22, and 25-26. Within certain embodiments of the invention, the polypeptides comprise up to 25 contiguous residues of SEQ ID NOs:4-6, 9-11, 14-17, 20-22, and 25-26. As disclosed in more detail below, these polypeptides can further comprise additional, non-ZS33LP polypeptide sequence(s).

Within the polypeptides of the present invention are polypeptides that comprise an epitope-bearing portion of a protein as shown in SEQ ID NOs:4-6, 9-11, 14-17, 20-22, and 25-26. An "epitope" is a region of a protein to which an antibody can bind. See, for example, Geysen et al., *Proc. Natl. Acad. Sci. USA* 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660-666, 1983. Antibodies that recognize short, linear epitopes are particularly useful in analytic and diagnostic applications that employ denatured protein, such as Western blotting (Tobin, *Proc. Natl. Acad. Sci. USA* 76:4350-4356, 1979), or in the analysis of fixed cells or tissue samples. Antibodies to linear epitopes are also useful for detecting fragments of ZS33LPs peptides, such as might occur in body fluids or cell culture media.

Antigenic, epitope-bearing polypeptides of the present invention are useful for raising antibodies, including monoclonal antibodies, that specifically bind to a ZS33LP. It is preferred that the amino acid sequence of the epitope-bearing polypeptide is selected to provide substantial solubility in aqueous solvents, that is the sequence includes relatively hydrophilic residues, and hydrophobic residues are substantially avoided, and are described herein. Of interest within the present invention are polypeptides that comprise the entire zsig33-linker, zsig33-beta, zsig33-gamma, zsig33-delta and zsig33-epsilon polypeptides or portions thereof.

Polypeptides of the present invention can be prepared with one or more amino acid substitutions, deletions or additions as compared to SEQ ID NOs:4-6, 9-11, 14-17, 20-22, and 25-26. These changes are preferably of a minor nature, that is conservative amino acid substitutions and other changes that do not significantly affect the folding or activity of the protein or polypeptide, and include amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20-25 residues, or an extension that facilitates purification (an affinity tag) as disclosed above. Two or more affinity tags may be used in combination. Polypeptides comprising affinity tags can further comprise a polypeptide linker and/or a proteolytic cleavage site between the zsig33-linker, zsig33-beta, zsig33-gamma, zsig33-delta, and zsig33-epsilon polypeptide and the affinity tag. Preferred cleavage sites include thrombin cleavage sites and factor Xa cleavage sites.

disclosed herein. When variants of SEQ ID NOs:4-6, 9-11, 14-17, 20-22, and 25-26 are employed, the resulting polypeptide will preferably be at least 80%, more preferably at least 90% or 95% identical to the corresponding region of SEQ ID NOs:4-6, 9-11, 14-17, 20-22, and 25-26. Percent sequence identity is determined by conventional methods. See, for example, Altschul et al., *Bull. Math. Bio.* 48:603-616, 1986, and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 1 (amino acids are indicated by the standard one-letter codes). The percent identity is then calculated as:

$$\left[\frac{\text{Total number of identical matches}}{\begin{array}{c}\text{length of the longer sequence plus}\\\text{the number of gaps introduced into the longer}\\\text{sequence in order to align the two sequences}\end{array}}\right]\times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Auxiliary domains can be fused to ZS33LP polypeptides to target them to specific cells, tissues, or macromolecules (e.g., collagen). For example, a ZS33LP or protein can be targeted to a predetermined cell type by fusing a zsig33-linker, zsig33-beta, zsig33-gamma, zsig33-delta, or zsig33-epsilon polypeptide to a ligand that specifically binds to a receptor on the surface of the target cell. In this way, polypeptides and proteins can be targeted for therapeutic or diagnostic purposes. A zsig33-linker, zsig33-beta, zsig33-gamma, zsig33-delta, or zsig33-epsilon polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

As disclosed above, the polypeptides of the present invention comprise at least nine contiguous residues of SEQ ID NOs:4-6, 9-11, 14-17, 20-22, and 25-26. These polypeptides may further comprise additional residues as shown in SEQ ID NOs:4-6, 9-11, 14-17, 20-22, and 25-26, a variant of SEQ ID NOs:4-6, 9-11, 14-17, 20-22, and 25-26 or another protein as The level of identity between amino acid sequences can be determined using the "FASTA" similarity search algorithm disclosed by Pearson and Lipman (*Proc. Natl. Acad. Sci. USA* 85:2444, 1988) and by Pearson (*Meth. Enzymol.* 183:63, 1990). Briefly, FASTA first characterizes sequence similarity by identifying regions shared by the query sequence (e.g., SEQ ID NOs:4-6, 9-11, 14-17, 20-22, and 25-26) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The present invention includes polypeptides having one or more conservative amino acid changes as compared with the amino acid sequence of SEQ ID NOs:4-6, 9-11, 14-17, 20-22, and 25-26. The BLOSUM62 matrix (Table 1) is an amino acid substitution matrix derived from about 2,000 local multiple alignments of protein sequence segments, representing highly conserved regions of more than 500 groups of related proteins (Henikoff and Henikoff, ibid.). Thus, the BLOSUM62 substitution frequencies can be used to define conservative amino acid substitutions that may be introduced into the amino acid sequences of the present invention. As used herein, the term "conservative amino acid substitution" refers to a substitution represented by a BLOSUM62 value of greater than −1. For example, an amino acid substitution is conservative if the substitution is characterized by a BLOSUM62 value of 0, 1, 2, or 3; Preferred conservative amino acid substitutions are characterized by a BLOSUM62 value of at least one 1 (e.g., 1, 2 or 3), while more preferred conservative amino acid substitutions are characterized by a BLOSUM62 value of at least 2 (e.g., 2 or 3).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-809, 1993; and Chung et al., *Proc. Natl. Acad. Sci. USA* 90:10145-10149, 1993). In a second method, translation is carried out in *Xenopus* oocytes by microinjection of mutated mRNA and chemically aminoacylated suppressor tRNAs (Turcatti et al., *J. Biol. Chem.* 271: 19991-19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993). Similarly, the d-stereoisomer of the amino acids can also be substituted.

Amino acid sequence changes are made in ZS33LP polypeptides so as to minimize disruption of higher order structure essential to biological activity. Amino acid residues that are within regions or domains that are critical to maintaining structural integrity can be determined. Within these regions one can identify specific residues that will be more or less tolerant of change and maintain the overall tertiary structure of the molecule. Methods for analyzing sequence structure include, but are not limited to, alignment of multiple sequences with high amino acid or nucleotide identity, secondary structure propensities, binary patterns, complementary packing, and buried polar interactions (Barton, *Current Opin. Struct. Biol.* 5:372-376, 1995 and Cordes et al., *Current Opin. Struct. Biol.* 6:3-10, 1996). In general, determination of structure will be accompanied by evaluation of activity of modified molecules. The effects of amino acid sequence changes can be predicted by, for example, computer modeling using available software (e.g., the Insight II® viewer and homology modeling tools; MSI, San Diego, Calif.) or determined by analysis of crystal structure (see, e.g., Lapthorn et al, *Nature* 369:455-461, 1994; Lapthorn et al., *Nat. Struct. Biol.* 2:266-268, 1995). Protein folding can be measured by circular dichroism (CD). Measuring and comparing the CD spectra generated by a modified molecule and standard molecule are routine in the art (Johnson, *Proteins* 7:205-214, 1990). Crystallography is another well known and accepted method for analyzing folding and structure. Nuclear magnetic resonance (NMR), digestive peptide mapping and epitope mapping are other known methods for analyzing folding and structural similarities between proteins and polypeptides (Schaanan et al., *Science* 257:961-964, 1992). Mass spectrometry and chemical modification using reduction and alkylation can be used to identify cysteine residues that are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). Alterations in disulfide bonding will be expected to affect protein folding. These techniques can be employed individually or in combination to analyze and compare the structural features that affect folding of a variant protein or polypeptide to a standard molecule to determine whether such modifications would be significant.

Hydrophilicity profiles of SEQ ID NOs:4, 9 and 14 have been performed. Particularly hydrophilic regions of these sequences are from residue 7 to residue 18 of SEQ ID NO:4, residue 14 to residue 21 of SEQ ID NO:9, and residue 7 to residue 16 of SEQ ID NO:14. Those skilled in the art will recognize that this hydrophilicity will be taken into account when designing alterations in the amino acid sequence of a zsig33-linker, zsig33-beta, zsig33-gamma, zsig33-delta, and zsig33-epsilon polypeptides, respectively, so as not to disrupt the overall profile.

Essential amino acids in the polypeptides of the present invention can be identified experimentally according to procedures known in the art, such as site-directed mutagenesis or alanine-scanning mutagenesis (Cunningham and Wells, *Science* 244, 1081-1085, 1989; Bass et al., *Proc. Natl. Acad. Sci.*

USA 88:4498-4502, 1991). In the latter technique, single alanine mutations are introduced at every residue in the molecule, and the resultant mutant molecules are tested for biological activity as disclosed below to identify amino acid residues that are critical to the activity of the molecule.

Multiple amino acid substitutions can be made and tested using known methods of mutagenesis and screening, such as those disclosed by Reidhaar-Olson and Sauer (*Science* 241: 53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed ZS33LP DNA and polypeptide sequences can be generated through DNA shuffling as disclosed by Stemmer, *Nature* 370:389-391, 1994 and Stemmer, *Proc. Natl. Acad. Sci. USA* 91:10747-10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

In many cases, the structure of the final polypeptide product will result from processing of the nascent polypeptide chain by the host cell, thus the final sequence of a ZS33LP produced by a host cell will not always correspond to the full sequence encoded by the expressed polynucleotide. For example, expressing the complete zsig33-linker, zsig33-beta, zsig33-gamma, zsig33-delta, and zsig33-epsilon sequence in a cultured mammalian cell is expected to result in removal of at least the secretory peptide, while the same polypeptide produced in a prokaryotic host would not be expected to be cleaved. Differential processing of individual chains may result in heterogeneity of expressed polypeptides.

Zsig33-linker, zsig33-beta, zsig33-gamma, zsig33-delta, and zsig33-epsilon proteins of the present invention are characterized by their activity, that is, modulation of gastrointestinal contractility, modulation of gastric motility, modulation of glucose uptake, modulation of insulin secretion, modulation of secretion of enzymes and/or hormones in the pancreas, or binding a ZS33LP binding partner. Biological activity of zsig33-linker, zsig33-beta, zsig33-gamma, and zsig33-delta, and zsig33-epsilon proteins is assayed using in vitro or in vivo assays designed to detect gastric emptying, contractility, glucose absorption, or binding proliferation, differentiation, migration or adhesion; or changes in cellular metabolism. Many suitable assays are known in the art, and representative assays are disclosed herein. Assays using cultured cells are most convenient for screening, such as for determining the effects of amino acid substitutions, deletions, or insertions. Assays can be performed using exogenously produced proteins, or may be carried out in vivo or in vitro using cells expressing the polypeptide(s) of interest. Assays can be conducted using zsig33-linker, zsig33-beta, zsig33-gamma, zsig33-delta, and zsig33-epsilon proteins alone or in combination with other growth factors, such as members of the VEGF family or hematopoietic cytokines (e.g., EPO, TPO, G-CSF, stem cell factor). Representative assays are disclosed below.

Mutagenesis methods as disclosed above can be combined with high volume or high-throughput screening methods to detect biological activity of ZS33LP variant polypeptides. Assays that can be scaled up for high throughput include mitogenesis assays, which can be run in a 96-well format. Mutagenized DNA molecules that encode active zsig33-linker, zsig33-beta, zsig33-gamma, zsig33-delta, and zsig33-epsilon polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptide fragments or variants of SEQ ID NOs:4-6, 9-11, 14-17, 20-22, and 25-26 that retain the activity of wild-type zsig33-linker, zsig33-beta, zsig-33 gamma, zsig33-delta, and zsig33-epsilon.

The present invention also provides polynucleotide molecules, including DNA and RNA molecules, that encode the zsig33-linker, zsig33-beta, zsig33-gamma, zsig33-delta, and zsig33-epsilon polypeptides disclosed above. Representative DNA sequences encoding the amino acid sequences of SEQ ID NOs:4-6, 9-11, 14-17, 20-22, and 25-26 are shown in SEQ ID NOs:3, 8, 13, 19, and 24, respectively. Those skilled in the art will readily recognize that, in view of the degeneracy of the genetic code, considerable sequence variation is possible among these polynucleotide molecules. SEQ ID NO:7 is a degenerate DNA sequence that encompasses all DNAs that encode the zsig33-linker peptide. SEQ ID NO:12 is a degenerate DNA sequence that encompasses all DNAs that encode the zsig33-beta peptide. SEQ ID NO:18 is a degenerate DNA sequence that encompasses all DNAs that encode the zsig33-gamma peptide. SEQ ID NO:23 is a degenerate DNA sequence that encompasses all DNAs that encode the zsig33-delta peptide. SEQ ID NO:27 is a degenerate DNA sequence that encompasses all DNAs that encode the zsig33-epsilon peptide. Those skilled in the art will recognize that the degenerate sequences of SEQ ID NOs:7, 12, 18, 23 and 27 also provide all RNA sequences encoding SEQ ID NOs:4, 9, 14, 20 and 25, respectively, by substituting U for T. Thus, zsig33-linker, zsig33-beta, zsig33-gamma, zsig33-delta, and zsig-33 epsilon polypeptide-encoding polynucleotides comprising nucleotides 1 to 72 of SEQ ID NO:3, or nucleotides 1 to 75 of SEQ ID NO:8, nucleotides 1 to 51 of SEQ ID NO:13, nucleotides 1 to 30 of SEQ ID NO:19, or nucleotide 1 to 45 of SEQ ID NO:24 and their RNA equivalents are contemplated by the present invention, as are segments of SEQ ID NOs:7, 12, 18, 23, and 27 encoding other zsig33-linker, zsig33-beta, zsig33-gamma, zsig33-delta, and zsig33-epsilon polypeptides disclosed herein. Table 2 sets forth the one-letter codes used within SEQ ID NOs:7, 12, 18, 23, and 27 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:7, 12, 18, 23, and 27 encompassing all possible codons for a given amino acid, are set forth in Table 3, below.

TABLE 3

| Amino Acid | One-Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NOs:4-6, 9-11, 14-17, 20-22, and 25-26. Variant sequences can be readily tested for functionality as described herein.

One of ordinary skill in the art will also appreciate that different species can exhibit preferential codon usage. See, in general, Grantham et al., *Nuc. Acids Res.* 8:1893-912, 1980; Haas et al. *Curr. Biol.* 6:315-24, 1996; Wain-Hobson et al., *Gene* 13:355-64, 1981; Grosjean and Fiers, *Gene* 18:199-209, 1982; Holm, *Nuc. Acids Res.* 14:3075-87, 1986; and Ikemura, *J. Mol. Biol.* 158:573-97, 1982. Introduction of preferred codon sequences into recombinant DNA can, for example, enhance production of the protein by making protein translation more efficient within a particular cell type or species. Therefore, the degenerate codon sequences disclosed in SEQ ID NOs:7, 12, 18, 23, and 27 serve as templates for optimizing expression of polynucleotides in various cell types and species commonly used in the art and disclosed herein.

Within preferred embodiments of the invention the isolated polynucleotides will hybridize to similar sized regions of SEQ ID NOs:3, 8, 13, 19, and 24, or a sequence complementary thereto under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of ZS33LP RNA. Stomach cells are preferred. Pancreas is another preferred source. Total RNA can be prepared using guanidine HCl extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-1412, 1972). Complementary DNA (cDNA) is prepared from poly(A)$^+$ RNA using known methods. In the alternative, genomic DNA can be isolated. Polynucleotides encoding zsig33-linker, zsig33-beta, zsig33-gamma, zsig33-delta, and zsig33-epsilon polypeptides are then identified and isolated by, for example, hybridization or PCR.

Those skilled in the art will recognize that the sequences disclosed in SEQ ID NOS:1 and 2 represent a single allele of human zsig33. Allelic variants of these sequences can be cloned by probing cDNA or genomic libraries from different individuals according to standard procedures.

The present invention further provides counterpart polypeptides and polynucleotides from other species ("orthologs"). Of particular interest are ZS33LP polypeptides from other mammalian species, including murine, porcine, ovine, bovine, canine, feline, equine, and other primate polypeptides. Orthologs of human zsig33-linker, zsig33-beta, zsig33-gamma, zsig33-delta, and zsig33-epsilon can be cloned using information and compositions provided by the present invention in combination with conventional cloning techniques. For example, a cDNA can be cloned using mRNA obtained from a tissue or cell type that expresses ZS33LP as disclosed above. A library is then prepared from mRNA of a positive tissue or cell line. A zsig33-linker, zsig33-beta, zsig-33 gamma, zsig33-delta, and zsig33-epsilon-encoding cDNA can then be isolated by a variety of methods, such as by probing with a complete or partial human cDNA or with one or more sets of degenerate probes based on the disclosed sequence. A cDNA can also be cloned using the polymerase chain reaction, or PCR (Mullis, U.S. Pat. No. 4,683,202), using primers designed from the representative human zsig33-linker, zsig33-beta, zsig33-gamma, zsig33-delta, and zsig33-epsilon sequences disclosed herein. Within an additional method, the cDNA library can be used to transform or transfect host cells, and expression of the cDNA of interest can be detected with an antibody to zsig33-linker, zsig33-beta, zsig33-gamma, zsig33-delta, and zsig33-epsilon polypeptides. Similar techniques can also be applied to the isolation of genomic clones.

For any ZS33LP polypeptide, including variants and fusion proteins, one of ordinary skill in the art can readily generate a fully degenerate polynucleotide sequence encoding that variant using the information set forth in Tables 2 and 3, above. Moreover, those of skill in the art can use standard software to devise zsig33-linker, zsig33-beta, zsig33-gamma, zsig33-delta, and zsig33-epsilon variants based upon the nucleotide and amino acid sequences described herein. The present invention thus provides a computer-readable medium encoded with a data structure that provides at least one of the following sequences: SEQ ID NO:1 to SEQ ID NO:28, and portions thereof. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP™ disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The zsig33-linker, zsig33-beta, zsig33-gamma, zsig33-delta, and zsig33-epsilon polypeptides of the present invention, including biologically active fragments, and fusion polypeptides can be produced according to conventional techniques using cells into which have been introduced an expression vector encoding the polypeptide. As used herein, "cells into which have been introduced an expression vector" include both cells that have been directly manipulated by the introduction of exogenous DNA molecules and progeny thereof that contain the introduced DNA. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology,* John Wiley and Sons, Inc., NY, 1987.

In general, a DNA sequence encoding a zsig33-linker, zsig33-beta, zsig33-gamma or zsig33-delta, and zsig33-epsilon polypeptide is operably linked to other genetic elements required for expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig33-linker, zsig33-beta, zsig33-gamma and zsig33-delta, and zsig33-epsilon polypeptide into the secretory pathway of a host cell, a secretory signal sequence (also known as a leader sequence, prepro sequence or pre sequence) is provided in the expression vector. The secretory signal sequence may be that of human zsig33 (i.e., from residue 1 to residue 23 of SEQ ID NO:2, or may be derived from another secreted protein (e.g., t-PA; see, U.S. Pat. No. 5,641,655) or synthesized de novo. The secretory signal sequence is operably linked to the zsig33-linker, zsig33-beta, zsig33-gamma or zsig33-delta, and zsig33-epsilon DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells can be used as hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1, ATCC No. CCL 61; or CHO DG44, Chasin et al., *Som. Cell. Molec. Genet.* 12:555, 1986) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, Manassas, Va. USA under accession numbers 98669 and 98668, respectively, and derivatives thereof.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

The adenovirus system (disclosed in more detail below) can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. In an alternative method, adenovirus vector-infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins can also be effectively obtained.

Insect cells can be infected with recombinant baculovirus, commonly derived from *Autographa californica* nuclear polyhedrosis virus (AcNPV) according to methods known in the art. Within a preferred method, recombinant baculovirus is produced through the use of a transposon-based system described by Luckow et al. (*J. Virol.* 67:4566-4579, 1993). This system, which utilizes transfer vectors, is commercially available in kit form (Bac-to-Bac™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a zsig33-linker, zsig33-beta, zsig-33 gamma, zsig33-delta, and zsig33-epsilon-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zsig33-linker, zsig33-beta, zsig33-gamma, zsig33-delta, and zsig33-epsilon protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, for example, U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally known in the art.

Other higher eukaryotic cells can also be used as hosts, including plant cells and avian cells. The use of *Agrobacterium rhizogenes* as a vector for expressing genes in plant cells has been reviewed by Sinkar et al., *J. Biosci.* (Bangalore) 11:47-58, 1987.

Fungal cells, including yeast cells, can also be used within the present invention. Yeast species of particular interest in this regard include *Saccharomyces cerevisiae, Pichia pastoris,* and *Pichia methanolica*. Methods for transforming *S. cerevisiae* cells with exogenous DNA and producing recombinant polypeptides therefrom are disclosed by, for example, Kaisaki, U.S. Pat. No. 4,599,311; Kaisaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kaisaki et al. (U.S. Pat. No. 4,931,373), which allows transformed cells to be selected by growth in glucose-containing media. Suitable promoters and terminators for use in yeast include those from glycolytic enzyme genes (see, e.g., Kaisaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-3465, 1986; Cregg, U.S. Pat. No. 4,882,279; and Raymond et al., *Yeast* 14, 11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zsig33-linker, zsig33-beta, zsig33-gamma, zsig33-delta, and zsig33-epsilon polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. Liquid cultures are provided with sufficient aeration by conventional means, such as shaking of small flasks or sparging of fermentors.

It is preferred to purify the polypeptides and proteins of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide or protein is substantially free of other polypeptides or proteins, particularly those of animal origin.

Expressed recombinant zsig33-linker, zsig33-beta, zsig33-gamma, zsig33-delta, and zsig33-epsilon proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

Zsig33-linker, zsig33-beta, zsig33-gamma, zsig33-delta, and zsig33-epsilon polypeptides can also be prepared through chemical synthesis according to methods known in the art, including exclusive solid phase synthesis, partial solid phase methods, fragment condensation or classical solution synthesis. In general, see, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

ZS33LPs may be monomers or multimers; glycosylated or non-glycosylated; pegylated or non-pegylated; amidated or non-amidated; sulfated or non-sulfated; and may or may not include an initial methionine amino acid residue. For example, ZS33LPs can also be synthesized by exclusive solid phase synthesis, partial solid phase methods, fragment condensation or classical solution synthesis. The peptides are preferably prepared by solid phase peptide synthesis, for example as described by Merrifield, *J. Am. Chem. Soc.* 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer & Rapp Chem. Pept. Prot. 3:3 (1986); and Atherton et al., Solid Phase Peptide Synthesis: *A Practical Approach*, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlortrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300-320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluoro-phosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyl-uronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, CH2Cl2 or mixtures thereof. The extent of completion of the coupling reaction can be monitored at each stage, e.g., by the ninhydrin reaction as described by Kaiser et al., *Anal. Biochem.* 34:595, 1970.

After the entire assembly of the desired peptide, the peptide-resin is cleaved with a reagent with proper scavengers. The Fmoc peptides are usually cleaved and deprotected by TFA with scavengers (e.g., H2O, ethanedithiol, phenol and thioanisole). The tBoc peptides are usually cleaved and deprotected with liquid HF for 1-2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury (II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

The activity of molecules of the present invention can be measured using a variety of assays that measure for example, modulation of gastrointestinal contractility, modulation of gastric motility, modulation of glucose uptake, modulation of insulin secretion, modulation of secretion of enzymes and/or hormones in the pancreas, or binding a ZS33LP binding partner. Of particular interest are changes in contractility of smooth muscle cells. For example, the contractile response of segments of mammalian duodenum or other gastrointestinal smooth muscles tissue (Depoortere et al., *J. Gastrointestinal Motility* 1:150-159, 1989, incorporated herein by reference). An exemplary in vivo assay uses an ultrasonic micrometer to measure the dimensional changes radially between commissures and longitudinally to the plane of the valve base (Hansen et al., *Society of Thoracic Surgeons* 60:S384-390, 1995).

Gastric motility is generally measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. A test food or liquid is radiolabeled with an isotope (e.g. $^{99m}$Tc), and after ingestion or administration, transit time through the gastrointestinal tract and gastric emptying are measured by visualization using gamma cameras (Meyer et al., *Am. J. Dig. Dis.* 21:296, 1976; Collins et al., *Gut* 24:1117, 1983; Maughan et al., *Diabet. Med.* 13 9 Supp. 5:S6-10, 1996 and Horowitz et al., *Arch. Intern. Med.* 145: 1467-1472, 1985). These studies may be performed before and after the administration of a promotility agent to quantify the efficacy of the drug.

In view of the tissue distribution observed for zsig33, agonists (including the natural ligand/substrate/cofactor/synthetic and naturally occurring peptides, and variants, etc.) and antagonists have enormous potential in both in vitro and in vivo applications. Compounds identified as ZS33LP agonists are useful for modulation of gastrointestinal contractility, modulation of gastric motility, modulation of glucose uptake, modulation of insulin secretion, modulation of secretion of enzymes and/or hormones in the pancreas, or binding a ZS33LP binding partner in vivo and in vitro. For example, agonist compounds are useful as components of defined cell culture media and regulate the uptake of nutrients, and thus are useful in specifically promoting the growth and/or development of gastrointestinal cells such as G cells, enterochromaffin cells and the epithelial mucosa of the stomach, duodenum, proximal jejunum, antrum and fundus. Additionally, ZS33LP polypeptides and ZS33LP agonists are useful as a research reagent, such as for the expansion, differentiation, growth factor and hormone secretion, and/or cell-cell interactions of tissues associated with the gastrointestinal system, brain, and/or central nervous system.

The family of gut-brain peptides has been associated with neurological and CNS functions. For example, NPY, a peptide with receptors in both the brain and the gut has been shown to stimulate appetite when administered to the central nervous system (Gehlert, *Life Sciences* 55(6):551-562, 1994). Motilin immunoreactivity has been identified in different regions of the brain, particularly the cerebellum, and in the pituitary (Gasparini et al., *Hum. Genetics* 94(6):671-674, 1994). Motilin has been found to coexist with neurotransmitter γ-aminobutyric acid in cerebellum (Chan-Patay, *Proc. Sym. 50th Anniv. Meet. Br. Pharmalog. Soc.:* 1-24, 1982). Physiological studies have provided some evidence that motilin has an affect on feeding behavior (Rosenfield et al., *Phys. Behav.* 39(6):735-736, 1987), bladder control, pituitary growth hormone release. Other gut-brain peptides, such as CCK, enkephalin, VIP and secretin have been shown to be involved in control of blood pressure, heart rate, behavior, and pain modulation, in addition to be active in the digestive system. Therefore, ZS33LPs, could be expected to have some neurological association.

Additionally, other members of the gut-brain peptides, such as CCK, gastrin, and the like, have been shown to modulate secretion of pancreatic enzymes and hormones. Thus, zsig33-beta and zsig33-gamma peptides can be used to modulate secretion of pancreatic enzymes and hormones.

Similarly, other members of this family are known to modulate the secretion of endogenous proteins, such as the manner in which glucagon modulates the secretion of insulin. ZS33LPs can be used to modulate the secretion of non-ZS33LP proteins such as, for example, GLP-1, growth hormone, somatostatin, and the like. One advantage of growth hormone secretagogues, in general, is their ability to amplify endogenous pulsatile growth hormone secretion while maintaining normal feedback mechanisms. Another important effect is the ability to restore serum insulin-like growth factor-1 (IGF-1) levels in elderly adults to concentrations similar to those of young adults. See Hansen, B. S. et al., *Eur. J. Endocrinol.* 141:180-189, 1999. Thus, ZS33LPs may be useful for modulating secretion of growth hormone and insulin-like growth factor 1.

Using site-specific changes in the amino acid and DNA sequences of the present invention analogs can be made that are either antagonists, agonists or partial agonists (Macielag et al., *Peptides: Chem. Struct. Biol.* pp. 659, 1996). Antagonists are useful for clinical conditions associated with gastrointestinal hypermotility such as diarrhea and Crohn's disease. Antagonists are also useful as research reagents for characterizing sites of ligand-receptor interaction.

Target cells for use in zsig33-linker, zsig33-beta, zsig33-gamma, zsig33-delta, and zsig33-epsilon activity assays include, without limitation, gastrointestinal cells (especially smooth muscle cells), pancreas cells (islets and beta cells), and pituitary cells. Endothelial cells and hematopoietic cells are derived from a common ancestral cell, the hemangioblast (Choi et al., *Development* 125:725-732, 1998).

Activity of ZS33LP proteins can be measured in vitro using cultured cells or in vivo by administering molecules of the claimed invention to an appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990), incorporation of radiolabelled nucleotides (as disclosed by, e.g., Raines and Ross, *Methods Enzymol.* 109:749-773, 1985; Wahl et al., *Mol. Cell. Biol.* 8:5016-5025, 1988; and Cook et al., *Analytical Biochem.* 179:1-7, 1989), incorporation of 5-bromo-2'-deoxyuridine (BrdU) in the DNA of proliferating cells (Porstmann et al., *J. Immunol. Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989; all incorporated herein by reference).

Zsig33-linker, zsig33-beta, zsig33-gamma, zsig33-delta, and zsig33-epsilon activity may also be detected using assays designed to measure zsig33-linker, zsig33-beta, zsig-33 gamma, zsig33-delta, and zsig33-epsilon-induced production of one or more additional growth factors or other macromolecules. Preferred such assays include those for determining the presence of hepatocyte growth factor (HGF), epidermal growth factor (EGF), transforming growth factor alpha (TGFα), interleukin-6 (IL-6), VEGF, acidic fibroblast growth factor (aFGF), angiogenin, and other macromolecules produced by the liver. Suitable assays include mitogenesis assays using target cells responsive to the macromolecule of interest, receptor-binding assays, competition binding assays, immunological assays (e.g., ELISA), and other formats known in the art.

Cell migration is assayed essentially as disclosed by Kähler et al. (*Arteriosclerosis, Thrombosis, and Vascular Biology* 17:932-939, 1997). A protein is considered to be chemotactic if it induces migration of cells from an area of low protein concentration to an area of high protein concentration. A typical assay is performed using modified Boyden chambers with a polystryrene membrane separating the two chambers (Transwell; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithelial-Mesenchymal Interaction in Cancer*, Birkhäuser Verlag, 1995, 235-248; Baatout, *Anticancer Research* 17:451-456, 1997).

Cell adhesion activity is assayed essentially as disclosed by LaFleur et al. (*J. Biol. Chem.* 272:32798-32803, 1997). Briefly, microtiter plates are coated with the test protein, non-specific sites are blocked with BSA, and cells (such as smooth muscle cells, leukocytes, or endothelial cells) are plated at a density of approximately $10^4$-$10^5$ cells/well. The wells are incubated at 37° C. (typically for about 60 minutes), then non-adherent cells are removed by gentle ishing. Adhered cells are quantitated by conventional methods (e.g., by staining with crystal violet, lysing the cells, and determining the optical density of the lysate). Control wells are coated with a known adhesive protein, such as fibronectin or vitronectin.

The activity of ZS33LP proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906-1912, 1992; Pitchford et al., *Meth. Enzymol.* 228:84-108, 1997; Arimilli et al., *J. Immunol. Meth.* 212:49-59, 1998; and Van Liefde et al., *Eur. J. Pharmacol.* 346:87-95, 1998. The microphysiometer can be used for assaying adherent or non-adherent eukaryotic or prokaryotic cells. By measuring extracellular acidification changes in cell media over time, the microphysiometer directly measures cellular responses to various stimuli, including ZS33LPs, their agonists, and antagonists. Preferably, the microphysiometer is used to measure responses of a ZS33LP-responsive eukaryotic cell, compared to a control eukaryotic cell that does not respond to ZS33LP. ZS33LP-responsive eukaryotic cells comprise cells into which a receptor for a ZS33LP has been transfected, thereby creating a cell that is responsive to a ZS33LP as well as cells naturally responsive to a ZS33LP. Differences, measured by a change in extracellular acidification in the response of cells exposed to a ZS33LP polypeptide, relative to a control not exposed to a ZS33LP, are a direct measurement of ZS33LP modulated cellular responses. Moreover, such ZS33LP-modulated responses can be assayed under a variety of stimuli. The present invention thus provides methods of identifying agonists and antagonists of ZS33LP proteins, comprising providing cells responsive to a ZS33LP polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change in extracellular acidification rate. Culturing a third portion of the cells in the presence of a ZS33LP protein and the absence of a test compound provides a positive control for the ZS33LP-responsive cells and a control to compare the agonist activity of a test compound with that of the ZS33LP polypeptide. Antagonists of ZS33LPs can be identified by exposing the cells to ZS33LPs protein in the presence and absence of the test compound, whereby a reduction in ZS33LP-stimulated activity is indicative of antagonist activity in the test compound.

Expression of ZS33LP polynucleotides in animals provides models for further study of the biological effects of overproduction or inhibition of protein activity in vivo. ZS33LP-encoding polynucleotides and antisense polynucleotides can be introduced into test animals, such as mice, using viral vectors or naked DNA, or transgenic animals can be produced.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161-89, 1994; and Douglas and Curiel, *Science & Medicine* 4:44-53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621-14624, 1988; Wu et al., *J. Biol. Chem.* 267:963-967, 1992; and Johnston and Tang, *Meth. Cell Biol.* 43:353-365, 1994.

Transgenic mice, engineered to express a zsig33-linker, zsig33-beta, zsig33-gamma, zsig33-delta, or zsig33-epsilon gene, and mice that exhibit a complete absence of zsig33-linker, zsig33-beta, zsig33-gamma, zsig33-delta, or zsig33-epsilon gene function, referred to as "knockout mice" (Snouwaert et al., *Science* 257:1083, 1992), can also be generated (Lowell et al., *Nature* 366:740-742, 1993). These mice can be employed to study the ZS33LP gene of interest and the protein encoded thereby in an in vivo system. Transgenic mice are particularly useful for investigating the role of ZS33LP proteins in early development in that they allow the identification of developmental abnormalities or blocks resulting from the over- or underexpression of a specific factor. See also, Maisonpierre et al., *Science* 277:55-60, 1997 and Hanahan, *Science* 277:48-50, 1997. Preferred promoters for transgenic expression include promoters from metallothionein and albumin genes.

Antisense methodology can be used to inhibit ZS33LP gene transcription to examine the effects of such inhibition in vivo. Polynucleotides that are complementary to a segment of a zsig33-linker, zsig33-beta, zsig-33 gamma, zsig33-delta, or zsig33-epsilon-encoding polynucleotides (e.g., a polynucleotide as set forth in SEQ ID NOs:3, 8, 13, 19, and 24) are designed to bind to zsig33-linker, zsig33-beta, zsig-33 gamma, zsig33-delta, or zsig33-epsilon-encoding mRNA and to inhibit translation of such mRNA. Such antisense oligonucleotides can also be used to inhibit expression of ZS33LP polypeptide-encoding genes in cell culture.

For pharmaceutical use, zsig33-linker, zsig33-beta, zsig33-gamma zsig33-delta, or zsig33-epsilon proteins are formulated for topical or parenteral, particularly intravenous or subcutaneous, delivery according to conventional methods. In general, pharmaceutical formulations will include a zsig33-linker, zsig33-beta, zsig33-gamma, zsig33-delta, or zsig33-epsilon zsig33-delta, or zsig33-epsilon zsig33-delta, or zsig33-epsilon polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. ZS33LPs will preferably be used in a concentration of about 10 to 100 µg/ml of total volume, although concentrations in the range of 1 ng/ml to 1000 µg/ml may be used. For topical application, such as for the promotion of wound healing, the protein will be applied in the range of 0.1-10 µg/cm$^2$ of wound area, with the exact dose determined by the clinician according to accepted standards, taking into account the nature and severity of the condition to be treated, patient traits, etc. Determination of dose is within the level of ordinary skill in the art. Dosing is daily or intermittently over the period of treatment. Intravenous administration will be by bolus injection or infusion over a typical period of one to several hours. Sustained release formulations can also be employed. In general, a therapeutically effective amount of ZS33LP is an amount sufficient to produce a clinically significant change in the treated condition, such as a clinically significant change in hematopoietic or immune function, a significant reduction in morbidity, or a significantly increased histological score.

ZS33LP proteins, agonists, and antagonists are useful for modulating the expansion, proliferation, activation, differentiation, migration, or metabolism of responsive cell types, which include both primary cells and cultured cell lines. Of particular interest in this regard are gastrointestinal smooth muscle cells, pancreas cells and pituitary cells. ZS33LP polypeptides are added to tissue culture media for these cell types at a concentration of about 10 pg/ml to about 100 ng/ml. Those skilled in the art will recognize that ZS33LP proteins can be advantageously combined with other growth factors in culture media.

Within the laboratory research field, ZS33LP proteins can also be used as molecular weight standards or as reagents in assays for determining circulating levels of the protein, such as in the diagnosis of disorders characterized by over- or under-production of ZS33LP proteins or in the analysis of cell phenotype.

ZS33LP proteins can also be used to identify inhibitors of their activity. Test compounds are added to the assays disclosed above to identify compounds that inhibit the activity of a ZS33LP protein. In addition to those assays disclosed above, samples can be tested for inhibition of ZS33LP activity within a variety of assays designed to measure receptor binding or the stimulation/inhibition of ZS33LP-dependent cellular responses. For example, ZS33LP-responsive cell lines can be transfected with a reporter gene construct that is responsive to a ZS33LP-stimulated cellular pathway. Reporter gene constructs of this type are known in the art, and generally comprise a response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. Candidate compounds, solutions, mixtures or extracts are tested for the ability to inhibit the activity of a ZS33LP on the target cells as evidenced by a decrease in ZS33LP stimulation of reporter gene expression. Assays of this type will detect compounds that directly block ZS33LP binding to cell-surface receptors, as well as compounds that block processes in the cellular pathway subsequent to receptor-ligand binding. In the alternative, compounds or other samples can be tested for direct blocking of ZS33LP binding to receptor using ZS33LP tagged with a detectable label (e.g., $^{125}$I, biotin, horseradish peroxidase, FITC, and the like). Within assays of this type, the ability of a test sample to inhibit the binding of labeled ZS33LP to the receptor is indicative of inhibitory activity, which can be confirmed through secondary assays. Receptors used within binding assays may be cellular receptors or isolated, immobilized receptors.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Antibodies are defined to be specifically binding if they bind to a ZS33LP polypeptide or protein with an affinity at least 10-fold greater than the binding affinity to control (non-ZS33LP) polypeptide or protein. The affinity of a monoclonal antibody can be readily determined by one of ordinary skill in the art (see, for example, Scatchard, *Ann. NY Acad. Sci.* 51: 660-672, 1949).

As used herein the term "binding partner" refers to any peptide that can bind specifically to the ZS33LP peptides of the present invention. Such peptides include, for example, receptors, receptor-like complementary molecules, and antibodies.

Some members of the gut peptide hormones have been shown to bind to G protein coupled receptors (GPCR). See Feighner, S. D. et al., *Science* 284: 2184-2188, 1999; and Kojima, M. et al., *Nature* 402: 656-660, 1999. Thus, the ZS33LP polypeptides of the present invention may bind a GPCR. Binding of the ZS33LP, or variant thereof, to the GPCR causes the G protein to release its bound GDP and to bind GTP, thus, activating the G protein. In general, activated G proteins then bind to an affector enzyme which catalyzes the formation of a second messenger. In the case of a ZS33LP binding to a GPCR the result of such second messenger can be measured by biological events such as, for example, gastric contractility, modulation of nutrient uptake, modulation of growth hormones, modulation of the secretion of digestive enzymes and hormones, and/or modulation of secretion of enzymes and/or hormones in the pancreas, as well as by other assays discussed herein.

Cells expressing functional GPCRs are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by calorimetric assay based on the metabolic breakdown of Alamar Blue™ (AccuMed, Chicago, Ill.) or 3-(4,5-dimethylthiazol-2-yl)-2,5-diphenyl tetrazolium bromide (MTT) (Mosman, *J. Immunol. Meth.* 65: 55-63, 1983).

Another assay of interest measures or detects changes in proliferation, differentiation, development and/or electrical coupling of muscle cells or myocytes. Additionally, the effects of ZS33LP polypeptides on cell-cell interactions of fibroblasts, myoblasts, nerve cells, white blood cells, immune cells, and tumor cells would be of interest to measure. Yet other assays examine changes in contractility, and secretion of hormones and enzymes. Alternative assays are also listed herein.

Additional assays provided by the present invention include the use of hybrid receptor polypeptides. These hybrid polypeptides fall into two general classes. Within the first class, the intracellular domain of a GPCR is joined to the ligand-binding domain of a second receptor. It is preferred that the second receptor be a G protein-coupled receptor, such as the motilin receptor, GPR38, or the zsig33 receptor, GHS-R. The hybrid receptor will further comprise transmembrane domains, which may be derived from either receptor. A DNA construct encoding the hybrid receptor is then inserted into a host cell. Cells expressing the hybrid receptor are cultured in the presence of motilin, or zsig33, respectively, and assayed for a response. This system provides a means for analyzing signal transduction mediated by the GPCR while using readily available ligands. This system can also be used to determine if particular cell lines are capable of responding to signals transduced by the GPCR. A second class of hybrid receptor polypeptides comprise the extracellular (ligand-binding) domain of a GPCR with a cytoplasmic domain of a second receptor, preferably a G protein-coupled receptor, and transmembrane domains. The transmembrane domains may be derived from either receptor. Hybrid receptors of this second class are expressed in cells known to be capable of responding to signals transduced by the second receptor. Together, these two classes of hybrid receptors enable the use of a broad spectrum of cell types within receptor-based assay systems.

Another assay uses cell lines expressing $G_{\alpha 16}$ and the calcium sensitive photoprotein, aequorin, in a screening system for agonist activity. This system (described by Stables, J. et al., *Anal. Biochem.* 252:115-126, 1997) uses the $G_{\alpha 16}$ protein to couple with any G protein-linked receptor. Binding the receptor results in an increase in intracellular calcium concentrations. The cells are pre-incubated in coelenterazine and the intracellular calcium reacts with aequorin (which has also been transfected into the cells) and coelenterazine resulting in a luminescent response. Cell lines from pituitary, hypothalamus, and pancreas would be useful for GHS-R in this assay.

The ZS33LP peptides of the present invention may bind the growth hormone secretagogue receptor. The release of growth hormone stimulates growth in many tissues and has effects on metabolic processes such as stimulating protein synthesis and free fatty acid mobilization as well as stimulating metabolism from a variety of energy sources from carbohydrates to fatty acids. Deficiency of growth hormone can result in medical disorders such as dwarfism. Growth hormone secretagogues are a class of small peptides which stimulate the release of growth hormone from pituitary cells by a mechanism of action other than that of GHRH, i.e., by binding a different receptor (GHS-R) in the pituitary and hypothalamus. Thus, the binding of this receptor can play a role in regulating growth hormone secretion in extraneuroendocrine activities, such as, for example, sleep and food intake. Therefore, the secretion of growth hormone can be regulated by the formation of a peptide-receptor complex between ZS33LP and GHS-R.

The binding of Zs33LP polypeptides to the GSH-R can be measured using a variety of assays that measure, for example, cell-cell interactions; ligand-receptor binding, and other biological functions associated with gut-hormone family members. Of particular interest is a change in gastrointestinal contractility, modulation of growth hormones, weight maintenance, and glucose absorption. Assays measuring ligand binding and gastrointestinal contractility are known in the art, and further described in the examples, herein. Additional assays for measuring growth hormone secretion, receptor binding, and body weight are described in Hansen, B. S. ibid.

Proteins, including peptides resulting from alternative splicing, of the present invention are useful for modulation of gastrointestinal contractility, modulation of nutrient uptake, modulation of growth hormones, modulation of the secretion of digestive enzymes and hormones, and/or modulation of secretion of enzymes and/or hormones in the pancreas, and gastric reflux either working in isolation, or in conjunction with other molecules (growth factors, cytokines, etc.) in tissues such as stomach, duodenum, jejunum, kidney, small intestine, skeletal muscle, lung, pituitary, hypothalamus, hippocampus, and central nervous system, in general. Alternative splicing of ZS33LP mRNA may be cell-type specific and confer activity to specific tissues.

The effects of ZS33LPs, their antagonists and agonists, on tissue contractility can be measured in vitro using a tensiometer with or without electrical field stimulation. Such assays are known in the art and can be applied to tissue samples, such as gastrointestinal and other contractile tissue samples, and can be used to determine whether ZS33LPs, their agonists or antagonists, enhance or depress contractility. Molecules of the present invention are hence useful for treating dysfunction associated with contractile tissues or can be used to suppress or enhance contractility in vivo. As such, molecules of the present invention have utility in treating gastrointestinal and growth related diseases.

The effect of the ZS33LPs, antagonists and agonists of the present invention on contractility of tissues including gastrointestinal tissues can be measured in a tensiometer that measures contractility and relaxation in tissues. See, Dainty et al., *J. Pharmacol.* 100:767, 1990; Rhee et al., *Neurotox.* 16: 179, 1995; Anderson, M. B., *Endocrinol.* 114:364-368, 1984; and Downing, S. J. and Sherwood, O. D, *Endocrinol.* 116: 1206-1214, 1985. For example, measuring vasodilatation of aortic rings is well known in the art. Briefly, aortic rings are taken from 4 month old Sprague Dawley rats and placed in a buffer solution, such as modified Krebs solution (118.5 mM NaCl, 4.6 mM KCl, 1.2 mM $MgSO_4.7H_2O$, 1.2 mM $KH_2PO_4$, 2.5 mM $CaCl_2.2H_2O$, 24.8 mM $NaHCO_3$ and 10 mM glucose). One of skill in the art would recognize that this method can be used with other animals, such as rabbits, other rat strains, Guinea pigs, and the like. The rings are then attached to an isometric force transducer (Radnoti Inc., Monrovia, Calif.) and the data recorded with a Ponemah physiology platform (Gould Instrument systems, Inc., Valley View, Ohio) and placed in an oxygenated (95% $O_2$, 5% $CO_2$) tissue bath containing the buffer solution. The tissues are adjusted to 1 gram resting tension and allowed to stabilize for about one hour before testing. The integrity of the rings can be tested with norepinepherin (Sigma Co., St. Louis, Mo.) and Carbachol, a muscarinic acetylcholine agonist (Sigma Co.). After integrity is checked, the rings are washed three times with fresh buffer and allowed to rest for about one hour. To test a sample for vasodilatation, or relaxation of the aortic ring tissue, the rings are contracted to two grams tension and allowed to stabilize for fifteen minutes. A ZS33LP sample is then added to 1, 2 or 3 of the 4 baths, without flushing, and tension on the rings recorded and compared to the control rings containing buffer only. Enhancement or relaxation of contractility by ZS33LPs, their agonists and antagonists is directly measured by this method, and it can be applied to other contractile tissues such as gastrointestinal tissues.

Potential uses of growth hormone are extensive and include treatment of diseases and conditions associated with bone formation (such as, for example, treatment of osteoporosis, acceleration of bone formation and repair, stimulating osteoblasts, bone remodeling and cartilage growth, and skeletal dysplasia); immunity (such as, for example, stimulating the immune system, treating immunosuppressed patients); obesity, and metabolic disorders (such as, for example, preventing catabolic side effects of glucocorticoids, treatment of obesity and growth retardation related to obesity, attenuation of protein catabolic responses after surgery, reducing cachexia and protein loss due to chronic illness such as cancer or AIDS); dwarfism (such as, for example, treating growth retardation and physiological short stature including growth hormone deficiency and chromic illness, and intrauterine growth retardation); wound healing (such as, for example, accelerating wound repair, accelerating recovery of burn patients and treating patients with delayed wound healing); reproduction (such as, for example, as an adjuvant treatment for ovulation induction); as well as conditions associated with stress; conditions associated with kidney and lung dysfunction; conditions associated with aging and the elderly, including, muscle strength, bone fragility and skin thickness; and neuroendocrine activities such as sleep. Thus, growth hormone secretagogues are useful to treat conditions associated with these disorders. Assays measuring the release of growth hormone are known in the art.

An association between gastrointestinal function and brain function has been observed for other hormones in this class. As an example, secretin infusion in autistic children resulted in amelioration of the gastrointestinal symptoms as well as a dramatic improvement in behavior (improved eye contact, alertness and expansion of expressive language). See Hovrath, K. et al., *J. Assoc. Acad. Minor Phys* 9(1):9-15, 1998. Similarly, a study of the upper gastrointestinal tract in autistic children with gastrointestinal symptoms showed that many had reflux esophagitis, chronic gastritis, and chronic duodenitis, as well as an elevated number of Paneth's cells in the duodenal crypts compared to non-autistic children. See Horvath, K. et al., *J. Pediatr.* 135(5):559-563, 1999. The administration of secretin to these autistic children resulted in increased pancreatico-biliary fluid output and higher fluid output. Gastrointestinal disorders, especially reflux esophagitis and disaccharide malabsoprtion may contribute to the behavioral problems of the non-verbal autistic patients. The observed increase in pancreatico-biliary secretion after secretin infusion suggests an upregulation of secretin receptors. As a member of the gut-hormone family of proteins, ZS33LP, by binding to its receptor, may have effects on neural development and/or utilization.

Molecules of the present invention can be used to identify and isolate other isoforms of GHS-R, or other G protein-coupled receptors, cell-surface binding proteins, or members of complement/anti-complement pairs involved in gut-hormone interactions. For example, ZS33LP can be immobilized on a column and membrane preparations run over the column (*Immobilized Affinity Ligand Techniques*, Hermanson et al., eds., Academic Press, San Diego, Calif., 1992, pp. 195-202). Proteins and peptides can also be radiolabeled (*Methods in Enzymol.*, vol. 182, "Guide to Protein Purification", M. Deutscher, ed., Acad. Press, San Diego, 1990, 721-37) or photoaffinity labeled (Brunner et al., *Ann. Rev. Biochem.* 62:483-514, 1993 and Fedan et al., *Biochem. Pharmacol.* 33:1167-80, 1984) and specific cell-surface proteins can be identified.

ZS33LPs, variants, and fragments thereof, may be useful as replacement therapy for disorders associated with cell-cell interactions, including disorders related to, for example, stimulation of gastrointestinal contractility, modulation of nutrient uptake, modulation of growth hormones, modulation of the secretion of digestive enzymes and hormones, and modulation of secretion of enzymes and/or hormones in the pancreas.

A less widely appreciated determinant of tissue morphogenesis is the process of cell rearrangement: Both cell motility and cell-cell adhesion are likely to play central roles in morphogenetic cell rearrangements. Cells need to be able to rapidly break and probably simultaneously remake contacts with neighboring cells. See Gumbiner, B. M., *Cell* 69:385-387, 1992. As a secreted protein in stomach, pituitary, hypothalamus, hippocampus, lung, kidney, duodenum, jejunum, small intestine, skeletal muscle, and pancreas, ZS33LPs may play a role in intercellular rearrangement in these and other tissues.

ZL33LP binding proteins, such as an anti-ZS33LP antibody, or a GPCR, may also be used within diagnostic systems for the detection of circulating levels of ZS33LP. Elevated or depressed levels of ligand or receptor polypeptides may be indicative of pathological conditions, including cancer.

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982, which is incorporated herein by reference). Of particular interest are generating antibodies to hydrophilic antigenic sites which include, for example, residues 6-22 of SEQ ID NO:4, residues 14-22 of SEQ ID NO:7, and residues 8 to 17 of SEQ ID NO:10. As would be evident to one of ordinary skill in the art, polyclonal antibodies can be generated from a variety of warm-blooded animals such as horses, cows, goats, sheep, dogs, chickens, rabbits, mice, and rats. The immunogenicity of a ZS33LP polypeptide may be increased through the use of an adjuvant such as alum (aluminum hydroxide) or Freund's complete or incomplete adjuvant. Polypeptides useful for immunization also include fusion polypeptides, such as fusions of a ZS33LP polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Alternative techniques for generating or selecting antibodies include in vitro exposure of lymphocytes to ZS33LP polypeptides, and selection of antibody display libraries in phage or similar vectors (e.g., through the use of immobilized or labeled ZS33LP polypeptides). Human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

A variety of assays known to those skilled in the art can be utilized to detect antibodies that specifically bind to ZS33LP polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to ZS33LP may be used for affinity purification of the protein, within diagnostic assays for determining circulating levels of the protein; for detecting or quantitating soluble ZS33LP polypeptide as a marker of underlying pathology or disease; for neutralizing the effects of ZS323LP, for immunolocalization within whole animals or tissue sections, including immunodiagnostic applications; for immunohistochemistry; and as antagonists to block protein activity in vitro and in vivo. Antibodies to ZS33LP may also be used for tagging cells that express ZS33LP; for affinity purification of ZS33LP polypeptides and proteins; in analytical methods employing FACS; for screening expression libraries; and for generating anti-idiotypic antibodies. Antibodies can be linked to other compounds, including therapeutic and diagnostic agents, using known methods to provide for targeting of those compounds to cells expressing receptors for ZS33LP. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies of the present invention may also be directly or indirectly conjugated to drugs, toxins, radionuclides and the like, and these conjugates used for in vivo diagnostic or therapeutic applications (e.g., inhibition of cell proliferation). See, in general, Ramakrishnan et al., *Cancer Res.* 56:1324-1330, 1996.

Polypeptides and proteins of the present invention can be used to identify and isolate receptors. ZS33LP receptors may be involved in growth regulation in the liver, blood vessel formation, and other developmental processes. For example, ZS33LP proteins and polypeptides can be immobilized on a column, and membrane preparations run over the column (as generally disclosed in *Immobilized Affinity Ligand Techniques*, Hermanson et al., eds., Academic Press, San Diego, Calif., 1992, pp. 195-202). Proteins and polypeptides can also be radiolabeled (*Methods Enzymol.*, vol. 182, "Guide to Protein Purification", M. Deutscher, ed., Academic Press, San Diego, 1990, 721-737) or photoaffinity labeled (Brunner et al., *Ann. Rev. Biochem.* 62:483-514, 1993 and Fedan et al., *Biochem. Pharmacol.* 33:1167-1180, 1984) and used to tag specific cell-surface proteins. In a similar manner, radiolabeled ZS33LP proteins and polypeptides can be used to clone the cognate receptor in binding assays using cells transfected with an expression cDNA library.

The peptides, variants, nucleic acid and/or antibodies of the present invention may be used in treatment of disorders associated with gastrointestinal contractility, secretion of digestive enzymes, hormones and acids, secretion of hormones in the pancreas and/or brain, gastrointestinal motility, recruitment of digestive enzymes; inflammation, particularly as it affects the gastrointestinal system; reflux disease and regulation of nutrient absorption. Specific conditions that will benefit from treatment with molecules of the present invention include, but are not limited to, diabetic gastroparesis, post-surgical gastroparesis, vagotomy, chronic idiopathic intestinal pseudo-obstruction and gastroesophageal reflux disease. Additional uses include, gastric emptying for radiological studies, stimulating gallbladder contraction and antrectomy.

The motor and neurological affects of molecules of the present invention make it useful for treatment of obesity and other metabolic disorders where neurological feedback modulates nutritional absorption. The molecules of the present invention are useful for regulating satiety, glucose absorption and metabolism, and neuropathy-associated gastrointestinal disorders.

Peptides of the present invention may be useful for evaluating functions of the hypothalamus-pituitary-adrenal axis by challenging the gastrointestinal system with zsig33-beta and zsig33-gamma peptides, including variants, and measuring gastric motility and contractility, modulation of nutrient uptake, modulation of the secretion of digestive enzymes and hormones, or modulation of secretion of enzymes and/or hormones in the pancreas.

Additionally, molecules of zsig33-beta and zsig33-gamma peptides may be used to detect or modulate the growth and/or differentiation of tumor cells which are expressing a receptor which binds to zsig33-beta and zsig33-gamma peptides. zsig33-beta and zsig33-gamma peptides can be labeled with radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. These labeled polypeptides can be applied in vitro or in vivo and are especially useful to identify receptors for zsig33-beta, zsig33-gamma, zsig33-delta, and zsig33-epsilon located on tumors in such tissues as, for example, stomach, brain, pancreas, kidney, duodenum, jejunum, and lung.

Molecules of the present invention are also useful as additives to anti-hypoglycemic preparations containing glucose and as adsorption enhancers for oral drugs which require fast nutrient action. Additionally, molecules of the present invention can be used to stimulate glucose-induced insulin release.

A common side effect experience by livestock raised in feedlot settings is failure to feed shortly after transport and/or post illness or change in environments. Often feed additives are used to stimulate gastric motility to encourage the animal to feed. Thus, molecules of the present invention can be used alone or in conjunction with existing therapies to stimulate hunger and feeding. Such results can be seen both in healthy and challenged animals.

Inhibitors of ZS33LP activity (ZS33LP antagonists) include anti-ZS33LP antibodies and soluble ZS33LP receptors, as well as other peptidic and non-peptidic agents (including ribozymes). Such antagonists can be used to block the effects of ZS33LP on cells or tissues. Of particular interest is the use of antagonists of ZS33LP activity in conditions such as Inflammatory or Irritable Bowel syndromes. Inhibitors can also be used in combination with other therapeutic agents.

In addition to antibodies, ZS33LP inhibitors include small molecule inhibitors and inactive receptor-binding fragments of ZS33LP polypeptides. Inhibitors are formulated for pharmaceutical use as generally disclosed above, taking into account the precise chemical and physical nature of the inhibitor and the condition to be treated. The relevant determinations are within the level of ordinary skill in the formulation art.

Alternatively, ZS33LP may activate the immune system which would be important in boosting immunity to infectious diseases, treating immunocompromised patients, such as HIV+ patients, or in improving vaccines. In particular, ZS33LP stimulation or expansion of hematopoietic cells, or their progenitors, would provide therapeutic value in treatment of bacterial or viral infection, and as an anti-neoplastic factor. ZS33LP stimulation of the immune response against viral and non-viral pathogenic agents (including bacteria, protozoa, and fungi) would provide therapeutic value in treatment of such infections by inhibiting the growth of such infections agents. Determining directly or indirectly the levels of a pathogen or antigen, such as a tumor cell, present in the body can be achieved by a number of methods known in the art and described herein.

The present invention includes a method of stimulating an immune response in a mammal exposed to an antigen or pathogen comprising the steps of: (1) determining directly or indirectly the level of antigen or pathogen present in said mammal; (2) administering a composition comprising a ZS33LP polypeptide in an acceptable pharmaceutical vehicle; (3) determining directly or indirectly the level of antigen or pathogen in said mammal; and (4) comparing the level of the antigen or pathogen in step 1 to the antigen or pathogen level in step 3, wherein a change in the level is indicative of stimulating an immune response. In another embodiment the ZS33LP composition is re-administered. In other embodiments, the antigen is a B cell tumor; a virus; a parasite or a bacterium.

In another aspect, the present invention provides a method of stimulating an immune response in a mammal exposed to an antigen or pathogen comprising: (1) determining a level of an antigen- or pathogen-specific antibody; (2) administering a composition comprising ZS33LP polypeptide in an acceptable pharmaceutical vehicle; (3) determining a post administration level of antigen- or pathogen-specific antibody; (4) comparing the level of antibody in step (1) to the level of antibody in step (3), wherein an increase in antibody level is indicative of stimulating an immune response.

Polynucleotides encoding ZS33LP polypeptides are useful within gene therapy applications where it is desired to increase or inhibit ZS33LP activity. If a mammal has a mutated or absent ZS33LP gene, a ZS33LP gene can be introduced into the cells of the mammal. In one embodiment, a gene encoding a ZS33LP polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-330, 1991); an attenuated adenovirus vector, such as the vector described by Stratford-Perricaudet et al., *J. Clin. Invest.* 90:626-630, 1992; and a defective adeno-associated virus vector (Samulski et al., *J. Virol.* 61:3096-3101, 1987; Samulski et al., *J. Virol.* 63:3822-3888, 1989). Within another embodiment, ZS33LP gene can be introduced in a retroviral vector as described, for example, by Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO Publication WO 95/07358; and Kuo et al., *Blood* 82:845, 1993. Alternatively, the vector can be introduced by liposome-mediated transfection ("lipofection"). Synthetic cationic lipids can be used to prepare liposomes for in vivo transfection of a gene encoding a marker (Feigner et al., *Proc. Natl. Acad. Sci. USA* 84:7413-7417, 1987; Mackey et al., *Proc. Natl. Acad. Sci. USA* 85:8027-8031, 1988). The use of lipofection to introduce exogenous genes into specific organs in vivo has certain practical advantages, including molecular targeting of liposomes to specific cells. Directing transfection to particular cell types is particularly advantageous in a tissue with cellular heterogeneity, such as the pancreas, liver, kidney, and brain. Lipids may be chemically coupled to other molecules for the purpose of targeting. Peptidic and non-peptidic molecules can be coupled to liposomes chemically. Within another embodiment, cells are removed from the body, a vector is introduced into the cells as a naked DNA plasmid, and the transformed cells are re-implanted into the body as disclosed above. Antisense methodology can be used to inhibit ZS33LP gene transcription in a patient as generally disclosed above.

ZS33LP polypeptides and anti-Zs33LP antibodies can be directly or indirectly conjugated to drugs, toxins, radionuclides and the like, and these conjugates used for in vivo diagnostic or therapeutic applications. For instance, polypeptides or antibodies of the present invention may be used to identify or treat tissues or organs that express a corresponding anti-complementary molecule (receptor or antigen, respectively, for instance). More specifically, ZS33LP polypeptides or anti-ZS33LP antibodies, or bioactive fragments or portions thereof, can be coupled to detectable or cytotoxic molecules and delivered to a mammal having cells, tissues, or organs that express the anti-complementary molecule.

Suitable detectable molecules can be directly or indirectly attached to the polypeptide or antibody, and include radionuclides, enzymes, substrates, cofactors, inhibitors, fluorescent markers, chemiluminescent markers, magnetic particles, and the like. Suitable cytotoxic molecules can be directly or indirectly attached to the polypeptide or antibody, and include bacterial or plant toxins (for instance, diphtheria toxin, *Pseudomonas* exotoxin, ricin, abrin, saporin, and the like), as well as therapeutic radionuclides, such as iodine-131, rhenium-188 or yttrium-90. These can be either directly attached to the polypeptide or antibody, or indirectly attached according to known methods, such as through a chelating moiety. Polypeptides or antibodies can also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

Polypeptide-toxin fusion proteins or antibody/fragment-toxin fusion proteins may be used for targeted cell or tissue inhibition or ablation, such as in cancer therapy. Of particular interest in this regard are conjugates of a ZS33LP polypeptide and a cytotoxin, which can be used to target the cytotoxin to a tumor or other tissue that is undergoing undesired angiogenesis or neovascularization. Target cells (i.e., those displaying the ZS33LP) bind the ZS33LP-toxin conjugate, which is then internalized, killing the cell. The effects of receptor-specific cell killing (target ablation) are revealed by changes in whole animal physiology or through histological examination. Thus, ligand-dependent, receptor-directed cyotoxicity can be used to enhance understanding of the physiological significance of a protein ligand. A preferred such toxin is saporin. Mammalian cells have no receptor for saporin, which is non-toxic when it remains extracellular.

In another embodiment ZS33LP-cytokine fusion proteins or antibody/fragment-cytokine fusion proteins may be used for enhancing in vitro cytotoxicity (for instance, that mediated by monoclonal antibodies against tumor targets) and for enhancing in vivo killing of target tissues (for example, blood and bone marrow cancers). See, generally, Hornick et al., *Blood* 89:4437-4447, 1997). In general, cytokines are toxic if administered systemically. The described fusion proteins enable targeting of a cytokine to a desired site of action, such as a cell having binding sites for ZS33LP, thereby providing an elevated local concentration of cytokine. Suitable cytokines for this purpose include, for example, interleukin-2 and granulocyte-macrophage colony-stimulating factor (GM-CSF). Such fusion proteins may be used to cause cytokine-induced killing of tumors and other tissues undergoing angiogenesis or neovascularization.

The bioactive polypeptide or antibody conjugates described herein can be delivered intravenously, intra-arterially or intraductally, or may be introduced locally at the intended site of action.

ZS33LPs of the present invention may be useful for evaluating functions of the hypothalamus-pituitary-adrenal axis by challenging the gastrointestinal system with ZS33LPs, including variants, and measuring gastric motility and contractility, modulation of nutrient uptake, modulation of growth hormones, modulation of the secretion of digestive enzymes and hormones, or modulation of secretion of enzymes and/or hormones in the pancreas.

The invention is further illustrated by the following non-limiting examples.

EXAMPLES

Example 1

Chemical Synthesis and Purification of Zsig33-linker, Zsig33-gamma, and Zsig33-delta, Peptides Zsig33-linker peptide, a peptide corresponding to amino acid residue 1 (Ala) to amino acid residue 24 (Arg) of SEQ ID NO: 4, is synthesized by solid phase peptide synthesis using a model 431A Peptide Synthesizer (Applied Biosystems/Perkin Elmer, Foster City, Calif.). Fmoc-Glutamine resin (0.63 mmol/g; Advanced Chemtech, Louisville, Ky.) is used as the initial support resin. 1 mmol amino acid cartridges (Anaspec, Inc. San Jose, Calif.) are used for synthesis. A mixture of 2(1-Hbenzotriazol-y-yl 1,1,3,3-tetrahmethylhyluronium hexafluorophosphate (HBTU), 1-hydroxybenzotriazol (HOBt), 2 m N,N-Diisolpropylethylamine, N-Methylpyrrolidone, Dichloromethane (all from Applied Biosystems/Perkin Elmer) and piperidine (Aldrich Chemical Co., St. Louis, Mo.), and used for synthesis reagents.

The Peptide Companion software (Peptides International, Louisville, Ky.) is used to predict the aggregation potential and difficulty level for synthesis for the zsig33-linker peptide. Synthesis is performed using single coupling programs, according to the manufacturer's specifications.

The peptide is cleaved from the solid phase following standard TFA cleavage procedure (according to Peptide Cleavage manual, Applied Biosystems/Perkin Elmer). Purification of the peptide is done by RP-HPLC using a C18, 10 µm semi-peparative column (Vydac, Hesperial, CA). Eluted fractions from the column are collected and analyzed for correct mass and purity by electrospray mass spectrometry. Two pools of the eluted material are collected. Purity is verified by mass spectrometry analysis.

A zsig33-gamma peptide corresponding to residues 1 to 17 of SEQ ID NO:10, and a zsig33-deltapeptide corresponding to residues 1 to 10 of SEQ ID NO:14 are synthesized by the same method.

Example 2

Chemical Synthesis and Purification of Zsig33-beta and Zsig33-epsilon Peptides

A zsig33-beta polypeptide, such as that shown in SEQ ID NOs:4, 5 and 6, is synthesized by solid phase peptide synthesis using the ABI/PE Peptide Synthesizer model 431A (Applied Biosytems/Perkin Elmer (ABI/PE, Foster City, Calif.).

Fmoc-Amide resin is used for synthesis of the active zsig33-beta peptide-amide and Fmoc-Asparagine resin are used for non-amidated zsig33-beta peptides. The Fmoc-Amide resin (0.68 mmol/g) and the Fmoc-Asparagine resin (0.75 mmol/g) are purchased from ABI/PE. The amino acids can be purchased from AnaSpec, Inc., San Jose, Calif. in pre-weighed, 1 mmol cartridges. All the reagents except piperidine are purchased from ABI/PE. The piperidine is purchased from Aldrich, St. Louis Mo. Synthesis procedure is taken from the ABI Model 431A manual. Double coupling cycles are used during the high aggregation portion of the sequence, as predicted by Peptide Companion software (Peptides International, Louisville, Ky.).

The peptides are cleaved from the solid phase following the standard TFA cleavage procedure as outlined in the Peptide Cleavage protocol manual published by ABI/PE. Purification of the peptides is by RP-HPLC using a C18, 10 mm preparative column. Eluted fractions from the column are collected and analyzed for correct mass and purity by electrospray mass spectrometry. The analysis results should indicate that the Zsig33-beta peptide is present and pure in one of the pools from the HPLC purification step. The pools containing each of the peptides is retained and lyophilized.

Post lyophilization, the zsig33-beta peptide is analyzed for purity using analytical HPLC. The analytical HPLC column used is a Vydac 10 cm, 5 um column. The analysis should result in 95% purity for Zsig33-beta peptides. These peptide is prepared for use in subsequent biological assays.

A zsig33-epsilon peptide corresponding to residues 1 to 13 of SEQ ID NO:17, is synthesized by the same method.

Example 3

Construction of Expression Plasmids

An expression plasmid containing all or part of a polynucleotide encoding a ZS33LP protein is constructed via homologous recombination. A fragment of ZS33LP cDNA is isolated by PCR using the polynucleotide sequence of the zsig33 secretion leader (nucleotides 50 to 118 of SEQ ID NO:1) followed by the polynucleotide sequence of SEQ ID NO: 3, 6, 9, 13, or 16 with flanking regions at the 5' and 3' ends corresponding to the vector sequences flanking the ZS33LP insertion point. The primers for PCR each include from 5' to 3' end: 40 bp of flanking sequence from the vector and 17 bp corresponding to the amino and carboxyl termini from the open reading frame of the ZS33LP.

Ten µl of the 100 µl PCR reaction mixture is run on a 0.8% low-melting-temperature agarose (SeaPlaque GTG®; FMC BioProducts, Rockland, Me.) gel with 1×TBE buffer for analysis. The remaining 90 µl of the reaction mixture is precipitated with the addition of 5 µl 1 M NaCl and 250 µl of absolute ethanol. The plasmid pZMP6, which has been cut with SmaI, is used for recombination with the PCR fragment. Plasmid pZMP6 is a mammalian expression vector containing an expression cassette having the cytomegalovirus immediate early promoter, multiple restriction sites for insertion of coding sequences, a stop codon, and a human growth hormone terminator; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae. It is constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain.

One hundred microliters of competent yeast (S. cerevisiae) cells are independently combined with 10 µl of the various DNA mixtures from above and transferred to a 0.2-cm electroporation cuvette. The yeast/DNA mixtures are electropulsed using power supply (BioRad Laboratories, Hercules, Calif.) settings of 0.75 kV (5 kV/cm), ∞ ohms, 25 µF. To each cuvette is added 600 µl of 1.2 M sorbitol, and the yeast is plated in two 300-µl aliquots onto two URA-D plates and incubated at 30° C. After about 48 hours, the Ura$^+$ yeast transformants from a single plate are resuspended in 1 ml H$_2$O and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid-ished glass beads and 200 µl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 µl ethanol (EtOH), followed by centrifugation for 10 minutes at 4° C. The DNA pellet is resuspended in 10 µl $H_2O$.

Transformation of electrocompetent *E. coli* host cells (Electromax DH10B™ cells; obtained from Life Technologies, Inc., Gaithersburg, Md.) is done with 0.5-2 ml yeast DNA prep and 40 µl of cells. The cells are electropulsed at 1.7 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is plated in 250-µl aliquots on four LB AMP plates (LB broth (Lennox), 1.8% Bacto™ Agar (Difco), 100 mg/L Ampicillin).

Individual clones harboring the correct expression constructs for zsig33-linker, zsig33-beta, zsig33-gamma, zsig33-delta, and zsig33-epsilon are identified by restriction digest to verify the presence of the correct insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct constructs are designated pZMP6/zsig33-linker, zsig33-beta, zsig-33 gamma, zsig33-delta, and zsig33-epsilon.

Example 4

Expression in Chinese Hamster Ovary Cells

CHO DG44 cells (Chasin et al., *Som. Cell. Molec. Genet.* 12:555-666, 1986) are plated in 10-cm tissue culture dishes and allowed to grow to approximately 50% to 70% confluency overnight at 37° C., 5% $CO_2$, in Ham's F12/FBS media (Ham's F12 medium (Life Technologies), 5% fetal bovine serum (Hyclone, Logan, Utah), 1% L-glutamine (JRH Biosciences, Lenexa, Kans.), 1% sodium pyruvate (Life Technologies)). The cells are then transfected with the plasmids from Example 3 by liposome-mediated transfection using a 3:1 (w/w) liposome formulation of the polycationic lipid 2,3-dioleyloxy-N-[2(sperminecarboxamido)ethyl]-N,N-dimethyl-1-propaniminium-trifluoroacetate and the neutral lipid dioleoyl phosphatidylethanolamine in membrane-filtered water (Lipofectamine™ Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). Zsig33-linker, zsig33-beta, and zsig-33 gamma/pZMP6 is diluted into 15-ml tubes to a total final volume of 640 µl with SF media. 35 µl of Lipofectamine™ is mixed with 605 µl of SF medium. The resulting mixture is added to the DNA mixture and allowed to incubate approximately 30 minutes at room temperature. Five ml of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 1% PSN media is added to each plate. The plates are incubated at 37° C. overnight, and the DNA:Lipofectamine™ mixture is replaced with fresh 5% FBS/Ham's media the next day. On day 3 post-transfection, the cells are split into T-175 flasks in growth medium. On day 7 post-transfection, the cells are stained with FITC-anti-CD8 monoclonal antibody (Pharmingen, San Diego, Calif.) followed by anti-FITC-conjugated magnetic beads (Miltenyi Biotec). The CD8-positive cells are separated using commercially available columns (mini-MACS columns; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 µl per well as necessary during this process. When a large percentage of the colonies in the plate are near confluency, 100 µl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5 mM β-mercaptoethanol, at 65° C., 10 minutes, then in 2.5% non-fat dry milk Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the antibody-HRP conjugate in 2.5% non-fat dry milk Western A buffer for 1 hour at room temperature on a rotating shaker. The filter is then ished three times at room temperature in PBS plus 0.01% Tween 20, 15 minutes per ish. The filter is developed with chemiluminescence reagents (ECL™ direct labelling kit; Amersham Corp., Arlington Heights, Ill.) according to the manufacturer's directions and exposed to film (Hyperfilm ECL, Amersham Corp.) for approximately 5 minutes. Positive clones are trypsinized from the 96-well dish and transferred to 6-well dishes in selection medium for scaleup and analysis by Western blot.

Example 5

Expression in Baby Hamster Kidney Cells

ZS33LPs are produced in BHK cells transfected with the plasmids prepared in Example 3. BHK 570 cells (ATCC CRL-10314) are plated in 10-cm tissue culture dishes and allowed to grow to approximately 50 to 70% confluence overnight at 37° C., 5% $CO_2$, in DMEM/FBS media (DMEM, Gibco/BRL High Glucose; Life Technologies), 5% fetal bovine serum (Hyclone, Logan, Utah), 1 mM L-glutamine (JRH Biosciences, Lenexa, Kans.), 1 mM sodium pyruvate (Life Technologies). The cells are then transfected with pZMP6/zsig33-linker, zsig33-beta, and zsig33-gamma by liposome-mediated transfection (using Lipofectamine™; Life Technologies), in serum free (SF) media (DMEM supplemented with 10 mg/ml transferrin, 5 mg/ml insulin, 2 mg/ml fetuin, 1% L-glutamine and 1% sodium pyruvate). The plasmid is diluted into 15-ml tubes to a total final volume of 640 µl with SF media. 35 µl of the lipid mixture is mixed with 605 µl of SF medium, and the resulting mixture is allowed to incubate approximately 30 minutes at room temperature. Five milliliters of SF media is then added to the DNA:lipid mixture. The cells are rinsed once with 5 ml of SF media, aspirated, and the DNA:lipid mixture is added. The cells are incubated at 37° C. for five hours, then 6.4 ml of DMEM/10% FBS, 1% PSN media is added to each plate. The plates are incubated at 37° C. overnight, and the DNA:lipid mixture is replaced with fresh 5% FBS/DMEM media the next day. On day 5 post-transfection, the cells are split into T-162 flasks in selection medium (DMEM+5% FBS, 1% L-Gln, 1% NaPyr, 1 μM methotrexate). Approximately 10 days post-transfection, two 150-mm culture dishes of methotrexate-resistant colonies from each transfection are trypsinized, and the cells are pooled and plated into a T-162 flask and transferred to large-scale culture.

Example 6

Protein Purification

Purification Conditions for ZS33LPs with N- and C-terminal EE Tags:

*E. coli, Pichia*, CHO and BHK cells are transfected with expression plasmids constructed in Example 3 and operably linked to a polynucleotide encoding a Glu-Glu tag (SEQ ID NO:28). ZS33LPs are expressed in the conditioned media of the *E. coli, Pichia methanolica*, and or chinese hamster ovary (CHO) cells. For ZS33LPs expressed in *E. coli* and *Pichia*, the media is not concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then concentrated to about 1.3 liters using a Millipore ProFlux A30 tangential flow concentrator fitted with a 3000 kDa cutoff Amicon (Bedford, Mass.) S10Y3 membrane. The concentrated material is again sterile-filtered with the Gelman filter, as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 50.0 ml sample of anti-EE Sepharose, prepared as described below, is added and the mixture gently agitated on a Wheaton (Millville, N.J.) roller culture apparatus for 18.0 h at 4° C.

The mixture is then poured into a 5.0×20.0 cm Econo-Column (Bio-Rad, Laboratories, Hercules, Calif.), and the gel is ished with 30 column volumes of phosphate buffered saline (PBS). The unretained flow-through fraction is discarded. Once the absorbance of the effluent at 280 nM is less than 0.05, flow through the column is reduced to zero, and the anti-EE Sepharose gel is ished with 2.0 column volumes of PBS containing 0.2 mg/ml of EE peptide (AnaSpec, San Jose, Calif.). The peptide that is used has the sequence GluTyrMet-ProValAsp. After 1.0 h at 4° C., flow is resumed and the eluted protein collected. This fraction is referred to as the peptide elution. The anti-EE Sepharose gel is then ished with 2.0 column volumes of 0.1 M glycine, pH 2.5, and the glycine ish is collected separately. The pH of the glycine-eluted fraction is adjusted to 7.0 by the addition of a small volume of 10×PBS and stored at 4° C. for future analysis, if needed.

The peptide elution is concentrated to 5.0 ml using a 15,000 molecular weight cutoff membrane concentrator (Millipore, Bedford, Mass.), according to the manufacturer's instructions. The concentrated peptide elution is then separated from free peptide by chromatography on a 1.5×50 cm Sephadex G-50 (Pharmacia, Piscataway, N.J.) column equilibrated in PBS at a flow rate of 1.0 mL/min using a BioCad Sprint HPLC (PerSeptive BioSystems, Framingham, Mass.). Two-ml fractions are collected and the absorbance at 280 nM monitored. The first peak of material absorbing at 280 nM and eluting near the void volume of the column is collected. This fraction is pure ZS33LP NEE or ZS33LP CEE. The pure material is concentrated as described above, analyzed by SDS-PAGE and Western blotting with anti-EE antibodies, aliquoted, and stored at −80° C. according to standard procedures.

Preparation of Anti-EE Sepharose:

A 100 ml bed volume of protein G-Sepharose (Pharmacia, Piscataway, N.J.) is ished 3 times with 100 ml of PBS containing 0.02% sodium azide using a 500 ml Nalgene 0.45 micron filter unit. The gel is ished with 6.0 volumes of 200 mM triethanolamine, pH 8.2 (TEA, Sigma, St. Louis, Mo.). and an equal volume of EE antibody solution containing 900 mg of antibody is added. After an overnight incubation at 4° C., unbound antibody is removed by ishing the resin with 5 volumes of 200 mM TEA as described above. The resin is resuspended in 2 volumes of TEA, transferred to a suitable container, and dimethylpimilimidate-2HCl (Pierce, Rockford, Ill.), dissolved in TEA, is added to a final concentration of 36 mg/ml of gel. The gel is rocked at room temperature for 45 min and the liquid is removed using the filter unit as described above. Nonspecific sites on the gel are then blocked by incubating for 10 min at room temperature with 5 volumes of 20 mM ethanolamine in 200 mM TEA. The gel is then ished with 5 volumes of PBS containing 0.02% sodium azide and stored in this solution at 4° C.

Purification of Untagged zsig33:

*E. coli, Pichia*, CHO and BHK cells are transfected with expression vectors containing the DNA sequence of SEQ ID NO:1, or a portion thereof. The procedure described below is used for protein expressed in conditioned medium of *E. coli, Pichia methanolica*, and Chinese hamster ovary (CHO) and baby hamster kidney (BHK) cells. For ZS33LP expressed in *E. coli* and *Pichia*, however, the medium is not be concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then be concentrated to about 1.3 liters using a Millipore ProFlux A30 tangential flow concentrator fitted with a 3000 kDa cutoff Amicon (Bedford, Mass.) S10Y3 membrane. The concentrated material is again sterile-filtered with the Gelman filter as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim).

Example 7

Construction of BaF3 Cells Expressing a GPCR

BaF3, an interleukin-3 (IL-3) dependent pre-lymphoid cell line derived from murine bone marrow (Palacios and Steinmetz, Cell 41: 727-734, 1985; Mathey-Prevot et al., Mol. Cell. Biol. 6: 4133-4135, 1986), is maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, pZP-5N/GHS-R cDNA (Example 5) is prepared and purified using a Qiagen Maxi Prep kit (Qiagen) as per manufacturer's instructions. BaF3 cells for electroporation are ished once in RPMI media and then resuspended in RPMI media at a cell density of $10^7$ cells/ml. One ml of resuspended BaF3 cells is mixed with 30 μg of a plasmid containing a GPCR (such as for example, GP38, or GHS-R) and transferred to separate disposable electroporation chambers (GIBCO BRL). Following a 15 minute incubation at room temperature the cells are given two serial shocks (800 lFad/300 V.; 1180 lFad/300 V.) delivered by an electroporation apparatus (CELL-PORATOR™; GIBCO BRL). After a 5 minute recovery time, the electroporated cells are transferred to 50 ml of complete media and placed in an incubator for 15-24 hours (37° C., 5% $CO_2$). The cells are then spun down and resuspended in 50 ml of complete media containing Geneticin™ (Gibco) selection (500 μg/ml G418) in a T-162 flask to isolate the G418-resistant pool. Pools of the transfected BaF3 cells, are assayed for ZS33LP binding capability as described below.

Example 8

Screening for GPCR Activity Using BaF3/GPCR Cells Using an Alamar Blue Proliferation Assay BaF3/GPCR cells are spun down and ished in mIL-3 free media 3 times to ensure the removal of the mIL-3. Cells are then counted in a hemacytometer, and plated in a 96-well format at 5000 cells per well in a volume of 100 μl per well using the mIL-3 free media.

Proliferation of the BaF3/GPCR cells is assessed using media containing synthesized ZS33LPs which have been diluted with mIL-3 free media to 50%, 25%, 12.5%, 6.25%, 3.125%, 1.5%, 0.75% and 0.375% concentrations. 100 μl of the diluted synthesized ZS33LP is added to the BaF3/GPCR cells. The total assay volume is 200 μl. Negative controls are run in parallel using mIL-3 free media only, without the addition of ZS33LP. The assay plates are incubated at 37° C., 5% $CO_2$ for 3 days at which time Alamar Blue (Accumed, Chicago, Ill.) is added at 20 μl/well. Alamar Blue gives a fluourometric readout based on number of live cells, and is thus a direct measurement of cell proliferation in comparison to a negative control. Plates are again incubated at 37° C., 5% $CO_2$ for 24 hours. Plates are read on the Fmax™ plate reader (Molecular Devices Sunnyvale, Calif.) using the SoftMax™ Pro program, at wavelengths 544 (Excitation) and 590 (Emmission).

A positive result is measured as approximately 4-fold over background when the BaF3 wild type cells do not proliferate at the same concentration. Additional variants, produced synthetically, or recombinantly, are also screened in this manner. Similarly, antibodies to ZS33LP may be tested in this manner for inhibition/antagonism of ZS33LPs.

Example 9

ZS33LP Anti-peptide Antibodies

Polyclonal anti-peptide antibodies are prepared by immunizing two female New Zealand white rabbits with the ZS33LPs (SEQ ID NOs: 4, 7, 10, 14, and 17). The peptides are synthesized as in Examples 1 and 2. The peptides are then conjugated to the carrier protein maleimide-activated keyhole limpet hemocyanin (KLH) through cysteine residues (Pierce, Rockford, Ill.). The rabbits are each given an initial intraperitoneal (IP) injection of 200 mg of conjugated peptide in Complete Freund's Adjuvant (Pierce, Rockford, Ill.) followed by booster IP injections of 100 mg conjugated peptide in Incomplete Freund's Adjuvant every three weeks. Seven to ten days after the administration of the third booster injection, the animals are bled and the serum is collected. The rabbits are then boosted and bled every three weeks.

The ZS33LP-specific antibodies are affinity purified from the rabbit serum using an CNBr-SEPHAROSE 4B peptide column (Pharmacia LKB) that is prepared using 10 mg of the ZS33LP peptide per gram CNBr-SEPHAROSE, followed by dialysis in PBS overnight. Peptide specific-ZS33LP antibodies are characterized by an ELISA titer check using 1 mg/ml of the appropriate peptide as an antibody target.

Example 10

Binding Studies of ZS33LP in situ

Ten week old Balb C male mice are anesthetized via intramuscular injection and tested for binding of ZS33LP peptides in vivo.

ZS33LPs are tested (i.e., SEQ ID NOs: 4, 7, 10, 14, and 17). A single glycine is used as a negative control. Additionally, a "scrambled" negative control is also tested. The peptides and controls are coupled to fluorescein isothiocyantate (FITC, Molecular Probes, Eugene, Oreg.) in the following manner: The peptides, glycine control and FITC are dissolved in 0.1 M sodium bicarbonate at pH 9.0 to a concentration of 2.0 mg/ml for the peptides and glycine control and 5 mg/ml for FITC, avoiding exposure of the FITC to strong light. The FITC/sodium bicarbonate solution is added to the peptides at a ratio of 1 mg FITC to 1 mg peptide or glycine control, and allowed to react in the dark at ambient room temperature for 1 hour. The FITC-conjugated peptides and glycine control are dialyzed in a 1 K dialysis membrane and 0.1 M sodium bicarbonate buffer at 4° C. The buffer is changed daily and unbound FITC in the post-dialyzed buffer is measured by HPLC. After six days, the buffer is changed to phosphate buffered saline (PBS) and dialyzed for two days followed by another change in PBS and dialyzed for another 2 days. Peptide- or glycine-bound FITC is determined by measuring the absorbance of the dialyzed FITC-bound material at 498 nm and dividing by the extinction coefficient of fluorescein, 0.083 μM. The molar ratio of fluorescein to peptide (mole FITC/mole peptide) is then determined.

The labeled peptides are administered via tail vein injections such that each mouse received 0.5 ml (0.5 mg) of labeled peptide which is allowed to circulate in the mice for 15 minutes following injection.

While under anesthesia the right atrium of each mouse is snipped to allow an exit path and 20 ml of PBS is injected into left ventricle and used to flush the circulatory system. The mice are then perfused with approximately 10 ml of formalin in neutral buffer (10% Neutral Buffered Formalin (NBF), Surgipath, Richmond, Ill.).

Tissues are harvested by dissection, and fixed overnight in 10% NBF before processing for histological evaluation. Tissues are processed in the V.I.P. 2000 (Miles, Inc., Elkhart, Ind.) resulting in Paraffin® infiltration of the tissue. The tissue/Paraffin® blocks are sliced into 5 μm sections in a Jung Biocut (Leica, Nussloch, Germany), placed on glass slides, and incubated at 60° C. for one hour to aid in adhering the tissue to the slide. The Paraffin® is removed by ishing the slides three times in 100% xylene for 5 minutes. The slides are then rehydrated by 2 ishes in 100% ethanol for 3 minutes; followed by one ish in 95% ethanol. The slides are allowed to dry and then mounted with 5 to 10 μl of antifade medium which is prepared by adding nine parts glycerol containing 2% DABCO (1,4-diazobicyclo-(2,2,2,)-octane, Sigma, St. Louis, Mo.), dissolved at 55-70° C. to one part 0.2 M Tris/HCL, pH 7.5 DAPI (Sigma, St. Louis, Mo.) or propididum iodide (0.5 μg/ml). See also Kievits, T. et al., *Cytogenet Cell Cenet* 53:134-136 (1990) for antifade medium. Slides are covered with cover slips and immediately examined by fluorescent microscopy at 495 nm.

Results are positive if the labeled ZS33LP shows increased fluorescence compared to the glycine and "scrambled" controls.

Example 11

Gastric Contractility

Two male Sprague-Dawley rats, approximately 12 weeks old (Harlan, Indianapolis, Ind.) are anesthetized with urethane and their stomachs are exposed through a small abdominal incision. Two 2.4 mm transducing crystals (Sonometrics, Ontario, Canada) are placed on the antral portion of the stomach such that circular contractions could be monitored as a change in the distance between the two crystals. The crystals are attached with VETBOND TISSUE ADHESIVE (3M, St. Paul, Minn.).

10 µl of 1 µM acetylcholine is applied topically to the stomach between the two crystals, and results in a rapid, but transient increase in the distance between two crystals. 10 µl of norepinephrine (NE) at 1 µM causes a reduction in the distance between the two crystals. The amplitude of the NE-induced decrease is approximately 50% of the acetylcholine-induced increase in distance. Both responses are transient.

A negative control of 10 µl of phosphate buffer solution (PBS) applied topically between the crystals has no effect.

A peptide corresponding to the amino acid sequence of SEQ ID NOs:4, 7, 10, 14, or 17 is dissolved in PBS) and 10 µl is applied topically for a final concentration of 1 µg, 10 µg or 100 µg. The ZS33LP at 1 µg induces a sustained, rhythmic increase and decrease in crystal distance.

Example 12

In vivo Glucose Absorption

Eight female ob/ob mice, approximately 6 weeks old (Jackson Labs, Bar Harbor, Me.) are adapted to a 4 hour daily feeding schedule for two weeks. After two weeks on the feeding schedule, the mice are give 100 µg of a peptide corresponding to the amino acid sequence as shown in SEQ ID NOs:4-6, 9-11, 14-17, 20-22, or 25-26 in 100 µl sterile 0.1% BSA by oral gavage, immediately after their eating period (post-prandially). Thirty minutes later, the mice are challenged orally with a 0.5 ml volume of 25% glucose. Retroorbital bleeds are done to determine serum glucose levels. Blood is drawn prior to peptide dosing, prior to oral glucose challenge, and at 1, 2, 4, and 20 hours following the glucose challenge.

When zsig33-beta, zsig33-gamma, zsig33-delta or zsig33-epsilon peptide is given orally at 100 µg, 30 minutes prior to an oral glucose challenge, an enhanced post-prandial glucose absorption is seen.

Example 13

Gastric Emptying

The effect of topically applied ZS33LP peptide (i.e. SEQ ID NOs:4-6, 9-11, 14-17, 20-22, and 25-26) on the transit of phenol red through the stomachs of fasted male Sprague-Dawley rats (Harlan, Indianapolis, Ind.) is evaluated. The rats (6 animals, 8 weeks old) are fasted 24 hrs prior to being anesthetized with urethane (0.5 ml/100 grams of 25% solution). After anesthetizing, the animals are orally gavaged with 1 ml of Phenol Red solution (50 mg/ml in 2% methylcellulose solution).

The stomach of each animal is exposed through a small abdominal incision and a ZS33LP or a 14 amino acid control of a scrambled sequence peptide is applied topically to the stomach five minutes following the gavage. The amount of Phenol Red remaining in the stomach is determined by measuring optical density of the extracted stomach contents 30 minutes after the gavage.

Reduction in the amount of Phenol Red remaining in the stomach by approximately 25% compared to a scrambled peptide, indicates that the ZS33LP enhances gastric emptying in these rats.

Example 14

In Vitro Binding Assay

In vitro binding of ZS33LP polypeptides is performed similar to a method described by Miller, P., et al., *Peptides* 16:11-18, 1995. Male Sprague-Dawley rats, approximately 12 weeks old (Harlan, Indianapolis, Ind.) are sacrificed by IV pentobarbital injections. Tissue from the antrum is removed and the mucosal and serosal layers are dissected away for the smooth muscle. Tissue is minced and homogenized (Brinkman Polytron, Luzern Switzerland), set at 10 for 60 seconds in 10 volumes of Tris-EDTA. The homogenate is centrifuged (1000×g for 15 minutes) and the supernatant is discarded. Pellets are ished and passed through a nylon mesh to remove tissue clumps. Membrane protein is quantified.

ZS33LP polypeptides (corresponding to SEQ ID NOs:4-6, 9-11, 14-17, 20-22, and 25-26) are iodinated by the chloramines-T method (See Boivin; M., et al., *J. Gastrointest. Motil.* 2:240-246, 1990). Iodinated peptides are purified by HPLC. Binding of $^{125}$ZS33LP on membrane extracts is performed in a volume of 890 µl of 50 µM Tris-HCl (pH8.00), 1 mM EDTA, 10 mM $MgCl_2$, and 2% BSA. The reaction is stopped by addition of 3 ml ice-cold Tris-EDTA buffer. Free and bound counts are separated by centrifugation at 1600×g for 10 minutes. Pellets are ished with 2.0 ml ice-cold Tris-EDTA buffer, and centrifuged again. Radioactivity if the pellet is determined by a gamma counter. Specific binding is calculated from total and nonspecific binding, determined in the absence and presence of $10^{-5}$ cold ZS33LP.

Example 15

Effects of ZS33LP on Body Weight, Food Intake, and Glucose Clearance

Female ob/ob mice, 8 weeks old, (Jackson Labs, Bar Harbor, Me.) are adapted to a special 4 hour daily feeding schedule for two weeks. They are fed ad libitum from 7:30-11:30 am daily. After two weeks on the feeding schedule, the mice are divided into six groups. Each group is given 1.0 mg/mouse of a ZS33LP (i.e., SEQ ID NO: 4, 7, 10, 14, or 17 or a scrambled sequence peptide for the negative control, in 100 ml sterile 0.1% BSQA by oral gavage just prior to receiving food, and, again at the end of the 4 hour feeding period. The mice are injected twice daily for fourteen days, during which time food intake and body weight is measured daily. On day 14, immediately after the second oral gavage of the zsig33-1 peptide, the mice are challenged orally with an 0.5 ml volume of 25% glucose. Retro-orbital bleeds are done to determine serum glucose levels immediately prior to administration of the ZS33LP or vehicle (t=30 min.), and also at 0, 1, 2, and 4 hours following the glucose challenge.

The effect on daily body weight or food intake measurements, or on glucose clearance is determined on day 14.

Example 16

Summary of Peptide Synthesis

Zsig33-like peptides corresponding to SEQ ID NOs: 4, 11, 14, 20 and 26 were synthesized with Fmoc chemistry on a model 431A Peptide Synthesizer (Applied Biosystems, Foster City, Calif.). Fmoc-Amide resin (Applied Biosystems) was used as the initial support resin for the zsig33-epsilon and zsig33-beta peptides. Fmoc-Lys(Boc) Wang resin (Anaspec, San Jose, Calif.) was used for the zsig33-delta and zsig33-gamma peptides. Fmoc-Arg(Pbf) Wang resin (Anaspec) was used for the zsig33-linker. Amino acid cartridges were obtained from Anaspec. A mixture of 2-(1H-Benzotriazol-1-yl)-1,1,3,3-Tetramethyluronium hexafluorophosphate (HBTU), 1-Hydroxybenzotriazole (HOBt), N,N-Diisopropylethylamine, N-Methylpyrrolidone, Dichloromethane (all from Applied Biosystems) and Piperidine (Aldrich Chemical Co., Milwaukee, Wis.), were used as synthesis reagents. The peptides were cleaved from the solid support with 95% TFA (J. T. Baker, Phillipsburg, N.J.). Purification of the peptides were done by RP-HPLC using a C18, 10 micron, 22×250 mm semi-preparative column (Vydac, Hesperia, Calif.). Eluted fractions from the column were collected and analyzed for correct mass and purity by electrospray mass spectrometry and by analytical RP-HPLC. Purified peptides were lyophilized to dryness.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. An isolated polynucleotide encoding a polypeptide, wherein the polypeptide consists of an amino acid sequence selected from the group consisting of:
   a) the amino acid sequence of SEQ ID NO:9;
   b) the amino acid sequence of SEQ ID NO:10; and
   c) the amino acid sequence of SEQ ID NO:11.

2. The isolated polynucleotide according to claim 1, wherein the amino acid sequence of the polypeptide consists of the amino acid sequence of SEQ ID NO:9.

3. The isolated polynucleotide according to claim 2, wherein the polypeptide has an addition, and wherein the addition is selected from the group consisting of:
   a) an amino-terminal extension;
   b) a carboxyl-terminal extension;
   c) a linker peptide; and
   d) an affinity tag.

4. The isolated polynucleotide according to claim 3, wherein the amino-terminal extension is an amino-terminal methionine.

5. The isolated polynucleotide according to claim 3, wherein the amino-terminal extension or the carboxyl-terminal extension is a cysteine.

6. An isolated polynucleotide consisting of residues 275 to 349 of SEQ ID NO: 1.

7. The isolated polynucleotide according to claim 6, wherein the polynucleotide encodes a polypeptide and wherein the polypeptide has an addition selected from the group consisting of:
   a) an amino-terminal extension;
   b) a carboxyl-terminal extension;
   c) a linker peptide; and
   d) an affinity tag.

8. The isolated polynucleotide according to claim 7, wherein the amino-terminal extension is an amino-terminal methionine.

9. The isolated polynucleotide according to claim 7, wherein the amino-terminal extension or the carboxyl-terminal extension is a cysteine.

10. The isolated polynucleotide according to claim 1, wherein the amino acid sequence of the polypeptide consists of the amino acid sequence of SEQ ID NO:10.

11. The isolated polynucleotide according to claim 10, wherein the polypeptide has an addition, and wherein the addition is selected from the group consisting of:
    a) an amino-terminal extension;
    b) a carboxyl-terminal extension;
    c) a linker peptide; and
    d) an affinity tag.

12. The isolated polynucleotide according to claim 11, wherein the amino-terminal extension is an amino-terminal methionine.

13. The isolated polynucleotide according to claim 11, wherein the amino-terminal extension or the carboxyl-terminal extension is a cysteine.

14. An isolated polynucleotide consisting of residues 275 to 346 of SEQ ID NO: 1.

15. The isolated polynucleotide according to claim 14, wherein the polynucleotide encodes a polypeptide and wherein the polypeptide has an addition selected from the group consisting of:
    a) an amino-terminal extension;
    b) a carboxyl-terminal extension;
    c) a linker peptide; and
    d) an affinity tag.

16. The isolated polynucleotide according to claim 15, wherein the amino-terminal extension is an amino-terminal methionine.

17. The isolated polynucleotide according to claim 15, wherein the amino-terminal extension or the carboxyl-terminal extension is a cysteine.

18. The isolated polynucleotide according to claim 1, wherein the amino acid sequence of the polypeptide consists of the amino acid sequence of SEQ ID NO:11.

19. The isolated polynucleotide according to claim 18, wherein the polypeptide has an addition, and wherein the addition is selected from the group consisting of:
    a) an amino-terminal extension;
    b) a carboxyl-terminal extension;
    c) a linker peptide; and
    d) an affinity tag.

20. The isolated polynucleotide according to claim 19, wherein the amino-terminal extension is an amino-terminal methionine.

21. The isolated polynucleotide according to claim 19, wherein the amino-terminal extension or the carboxyl-terminal extension is a cysteine.

22. An isolated polynucleotide consisting of residues 275 to 343 of SEQ ID NO: 1.

23. The isolated polynucleotide according to claim 22, wherein the polynucleotide encodes a polypeptide and wherein the polypeptide has an addition selected from the group consisting of:
   a) an amino-terminal extension;
   b) a carboxyl-terminal extension;
   c) a linker peptide; and
   d) an affinity tag.

24. The isolated polynucleotide according to claim 23, wherein the amino-terminal extension is an amino-terminal methionine.

25. The isolated polynucleotide according to claim 23, wherein the amino-terminal extension or the carboxyl-terminal extension is a cysteine.

* * * * *